United States Patent
Taoka et al.

(10) Patent No.: US 8,067,640 B2
(45) Date of Patent: Nov. 29, 2011

(54) METHOD FOR THE SEPARATION OF INTERMEDIATES WHICH MAY BE USED FOR THE PREPARATION OF ESCITALOPRAM

(75) Inventors: Naoki Taoka, Kobe (JP); Takahisa Kato, Akashi (JP); Shogo Yamamoto, Kobe (JP); Takashi Yoshida, Kobe (JP); Toshihiro Takeda, Takasago (JP); Yasuyoshi Ueda, Himeji (JP); Hans Petersen, Vanløse (DK); Robert Dancer, Hvidovre (DK); Haleh Ahmadian, Solrød Strand (DK); Lars O. Lyngso, Bagsværd (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 12/781,026

(22) Filed: May 17, 2010

(65) Prior Publication Data

US 2011/0065937 A1    Mar. 17, 2011

Related U.S. Application Data

(63) Continuation of application No. 10/524,937, filed as application No. PCT/DK03/00537 on Aug. 12, 2003, now abandoned.

(60) Provisional application No. 60/403,088, filed on Aug. 12, 2002.

(30) Foreign Application Priority Data

Aug. 12, 2002    (DK) ................. 2002 01201

(51) Int. Cl.
*C07C 57/00*    (2006.01)

(52) U.S. Cl. ........ 564/304; 564/302; 564/303; 568/811; 558/44; 558/415; 558/422; 435/280

(58) Field of Classification Search ........... None
See application file for complete search history.

(56) References Cited

U.S. PATENT DOCUMENTS

| | | | |
|---|---|---|---|
| 4,136,193 A | 1/1979 | Bogeso et al. | |
| 4,650,884 A | 3/1987 | Bogeso | |
| 4,943,590 A * | 7/1990 | Boegesoe et al. | 514/469 |
| 5,219,743 A | 6/1993 | Takano et al. | |
| 6,407,267 B1 * | 6/2002 | Rock et al. | 549/467 |
| 6,551,806 B1 | 4/2003 | Strurmer | |

FOREIGN PATENT DOCUMENTS

| | | |
|---|---|---|
| EP | 0 171 943 | 11/1988 |
| EP | 0 347 066 | 12/1989 |
| WO | 98/00081 | 1/1998 |
| WO | 98/19511 | 5/1998 |
| WO | 98/19512 | 5/1998 |
| WO | 99/00210 | 1/1999 |
| WO | 99/30548 | 6/1999 |
| WO | 00/11926 | 3/2000 |
| WO | 00/12044 | 3/2000 |
| WO | 00/13648 | 3/2000 |
| WO | 00/23431 | 4/2000 |
| WO | 00/44738 | 8/2000 |
| WO | 01/02383 | 1/2001 |
| WO | 01/43525 | 6/2001 |
| WO | 01/51478 | 7/2001 |

(Continued)

OTHER PUBLICATIONS

Specialty Chemicals Magazine, Apr. 2003, 36-38.
Bisht et al., "Enzyme-mediated regioselective acylations of sophorolipids", J. Org. Chem. 64, p. 780-789, 1999.
Danieli et al., "Application of lipase-catalyzed regioselective esterification in the preparation of digitonin derivatives", Journal of Natural Products, 62, p. 670-673, 1999.

(Continued)

*Primary Examiner* — Sudhakar Katakam
(74) *Attorney, Agent, or Firm* — Stephen G. Kalinchak; Mary Catherine Di Nunzio

(57) ABSTRACT

The present invention relates to a novel method for the preparation of diol intermediates having the formula (II) and/or the opposite enantiomer of an acylated diol having the formula (IV) useful for the preparation of escitalopram involving selective enzymatic acylation or deacylation.

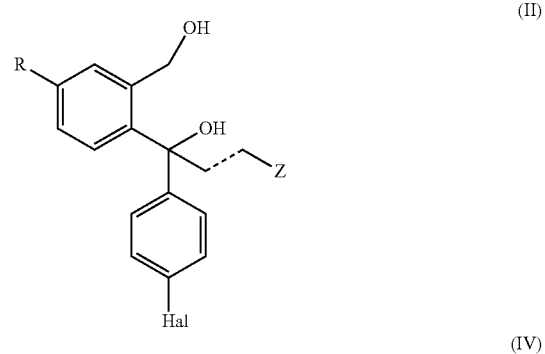

(II)

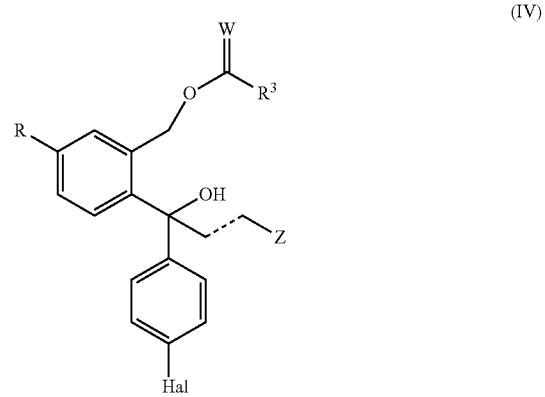

(IV)

7 Claims, No Drawings

FOREIGN PATENT DOCUMENTS

| | | |
|---|---|---|
| WO | 01/66536 | 9/2001 |
| WO | 01/68629 | 9/2001 |
| WO | 01/68630 | 9/2001 |
| WO | 01/68631 | 9/2001 |
| WO | 01/68632 | 9/2001 |
| WO | 02/16342 | 2/2002 |
| WO | 03/000672 | 1/2003 |
| WO | 03/006449 | 1/2003 |
| WO | 03/051861 | 6/2003 |
| WO | 03/087081 A1 | 10/2003 |

OTHER PUBLICATIONS

Liang et al., "Chemoenzymatic synthesis of enantiopure 1-azafagomine", Journal of Organic Chemistry, 64, p. 8485-8488, 1999.

Yee et al., "Practical synthesis of an enantiomerically pure trans-4,5 disubstituted 2-pyrrolidinone via enzymatic resolution. Preparation of the LTB4 inhibitor BIRZ-227." Journal of Organic Chemistry, 63:2, p. 326-330, 1998.

* cited by examiner

METHOD FOR THE SEPARATION OF INTERMEDIATES WHICH MAY BE USED FOR THE PREPARATION OF ESCITALOPRAM

CROSS REFERENCE TO RELATED APPLICATIONS

This application is a continuation of U.S. Ser. No. 10/524,937, filed Feb. 16, 2006 now abandoned, which is a §371 national stage of PCT International Application No. PCT/DK03/00537, filed Aug. 12, 2003, on behalf of H. Lundbeck A/S, which claims priority of U.S. Ser. No. 60/403,088 filed Aug. 12, 2002 and Danish Application No. PA 200201201, filed Aug. 12, 2002, the contents of each of which are hereby incorporated by reference into the subject application.

The present invention relates to a novel method for the preparation of optically active intermediates useful for the preparation of escitalopram involving selective enzymatic acylation or deacylation.

BACKGROUND OF THE INVENTION

Citalopram is a well-known antidepressant drug that has now been on the market for some years.

It is a selective, centrally acting serotonin (5-hydroxytryptamine; 5-HT) reuptake inhibitor, accordingly having antidepressant activities.

Citalopram was first disclosed in DE 2,657,013, corresponding to U.S. Pat. No. 4,136,193. This patent publication i.a. outlines a process for preparation of citalopram from the corresponding 5-bromo-derivative by reaction with cuprous cyanide in a suitable solvent and by alkylation of 5-bromophtalane.

U.S. Pat. No. 4,943,590 corresponding to EP-B1-347 066 describes two processes for the preparation of escitalopram (S-enantiomer of citalopram).

Both processes use the racemic diol having the formula

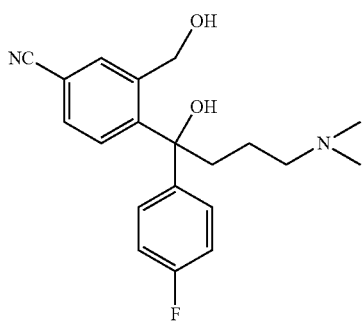

as starting material. According to the first process, the diol of formula (I) is reacted with an enantiomerically pure acid derivative, such as (+) or (−)-α-methoxy-α-trifluoromethyl-phenylacetyl chloride to form a mixture of diastereomeric esters, which are separated by HPLC or fractional crystallization, whereupon the ester with the correct stereochemistry is enantioselectively converted into escitalopram. According to the second process, the diol of formula (II) is separated into the enantiomers by stereoselective crystallization with an enantiomerically pure acid such as (+)-di-p-toluoyltartaric acid, whereupon the S-enantiomer of the diol of the formula (A) is enantioselectively converted to escitalopram.

Escitalopram has now been developed as an antidepressant. Hence, there is a desire for an improved method for preparation of escitalopram.

It has now been found that the S-enantiomer of the diol of formula (I) above as well as acylated derivatives thereof may be prepared by selective enzymatic acylation of the primary hydroxyl group in the racemic diol to obtain S-diol or an acylated derivative thereof with high optical purity and further that the enantiomers obtained may be separated by a series of isolation and purification operations.

The Invention

Accordingly, the present invention relates to a novel process for the preparation of the S- or R-enantiomer of a diol having the formula

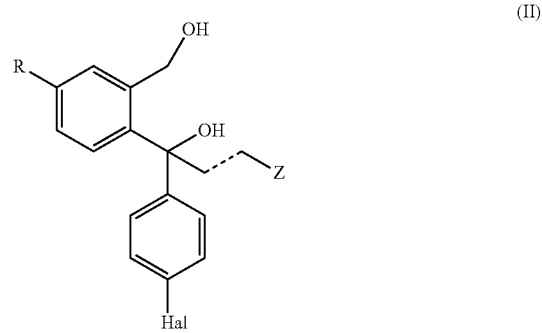

wherein R is cyano or a group which may be converted to a cyano group, Z is a group —$CH_2$—N(R'R") wherein R' and R" are $C_{1-6}$-alkyl, or R' and R" are connected to each other to form a cyclic structure including the N-atom to which they are attached, or Z is a group which may be converted to a dimethylaminomethyl group, the dotted line represents a double or a single bond and Hal is halogen or a salt thereof, and/or the opposite enantiomer of an acylated diol having the formula

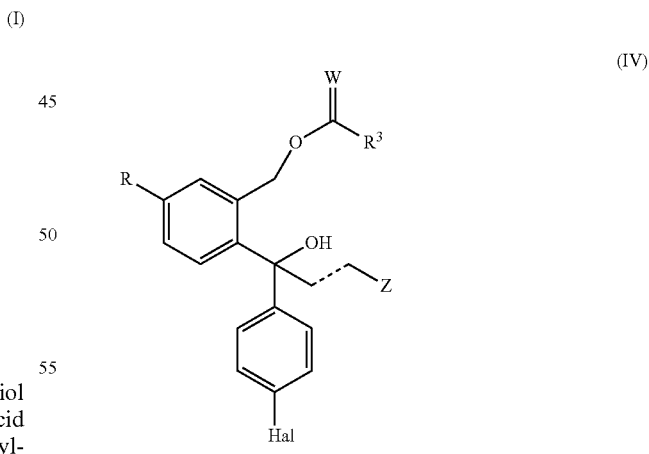

wherein R, Z, the dotted line and Hal are as defined above, W is O or S, and $R^3$ is —Y—$R^1$, wherein $R^1$ is $C_{1-10}$-alkyl, $C_{2-10}$-alkenyl or $C_{2-10}$-alkynyl all of which may optionally be substituted one or more times with substituents selected from $C_{1-10}$-alkoxy, $C_{1-10}$-alkylthio, hydroxy, halogen, amino, nitro, cyano, $C_{1-10}$-alkylamino, di-($C_{1-10}$-alkyl)amino, aryl, aryloxy, arylthio and heteroaryl, or $R^1$ is aryl; wherein any of the aryl and heteroaryl groups may optionally be substituted one or more times with substituents selected from $C_{1-10}$-alkyl, $C_{2-10}$-alkenyl, $C_{2-10}$-alkynyl, $C_{1-10}$-alkoxy, $C_{1-10}$-alkylthio, hydroxy, halogen, amino, nitro, cyano, $C_{1-10}$-alkylamino and di-($C_{1-10}$-alkyl)amino and Y is a bond, O, S or NH, or a salt thereof, comprising a) subjecting a racemic compound of formula

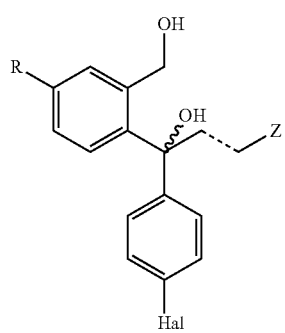
(II)

wherein R, Z, the dotted line and Hal are as defined above, to selective enzymatic acylation using an acylating agent having the formula

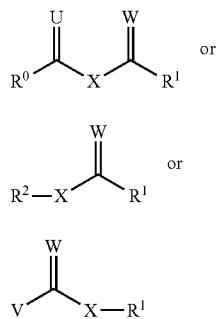
(IIIa)

or (IIIb)

or (IIIc)

or an isocyanate having the formula $R^1$—N=C=O or an isothiocyanate having the formula $R^1$—N=C=S;

wherein X is O or S; W is O or S; U is O or S, V is halogen and $R^0$ is $C_{1-10}$-alkyl, $C_{2-10}$-alkenyl or $C_{2-10}$-alkynyl all of which may optionally be substituted one or more times with substituents selected from $C_{1-10}$-alkoxy, $C_{1-10}$-alkylthio, hydroxy, halogen, amino, nitro, cyano, $C_{1-10}$-alkylamino, di-($C_{1-10}$-alkylamino, aryl, aryloxy, arylthio and heteroaryl, or $R^0$ is aryl, wherein any of the aryl and heteroaryl groups may optionally be substituted one or more times with substituents selected from $C_{1-10}$-alkyl, $C_{2-10}$-alkenyl, $C_{2-10}$-alkynyl, $C_{1-10}$alkoxy, $C_{1-10}$-alkylthio, hydroxy, halogen, amino, nitro, cyano, $C_{1-10}$-alkylamino and di-($C_{1-10}$-alkyl)amino;

$R^1$ is as defined for $R^0$;

$R^2$ is as defined for $R^0$, or $R^2$ is a suitable leaving group;

or $R^0$ and $R^1$ together form a chain of 3 to 5 carbon atoms;

provided that W and U are not S when X is S; to form a mixture of the starting material of formula (II) in either the R- or the S-form and the opposite enantiomer of the acylated diol having the formula

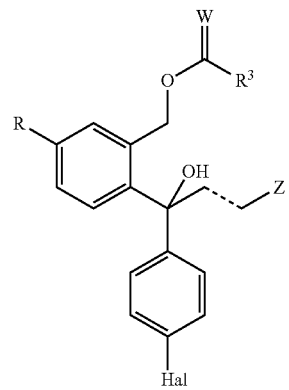
(IV)

wherein R, W, Hal, $R^3$, the dotted line and Z are as defined above; or b) subjecting a racemic compound of formula

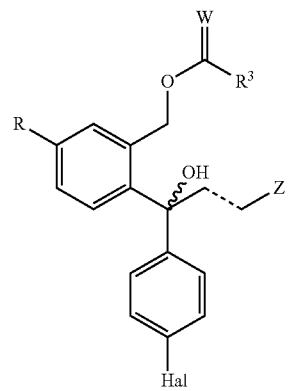
(IV)

wherein R, Z, W, Hal, the dotted line and $R^3$ are as defined above; to selective enzymatic deacylation to form a mixture of deacylated compound of formula

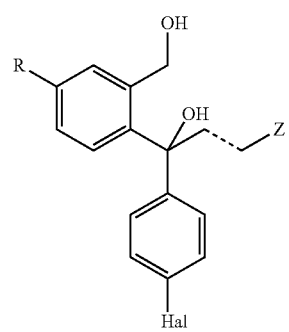
(II)

wherein R, Hal, the dotted line and Z are as defined above in either the R- or the S-form and the acylated starting material of formula (IV) in the form of the opposite enantiomer;

optionally followed by, in either order, isolation of the S- or R-enantiomer of the compound of formula (II) and/or the opposite enantiomer of the compound of formula (IV) or a salt thereof.

The invention also relates to methods for the separation of mixtures of an enantiomer of formula (IV) from the opposite enantiomer of formula (II) and to the R- and S-enantiomers of the compounds of formula (IV) above.

Finally, the invention relates to a method for the preparation of escitalopram and racemic citalopram from the enantiomers of a compound of formula (II) obtained by the selective enzymatic acylation or deacylation according to the invention, or the enantiomers of the optically active acyl derivative of formula (IV) obtained by the selective enzymatic acylation or deacylation according to the invention.

DETAILED DESCRIPTION OF THE INVENTION

When used in connection with the compounds of formula (II), (IV) and (V), the terms "enantiomer", "R-enantiomer", "S-enantiomer", "R-form", "S-form", "R-diol" and "S-diol" refer to the orientation of the groups around the carbon atom to which the 4-Hal-phenyl group is attached.

The present invention thus relates in one embodiment to a selective enzymatic acylation as above and in another embodiment to selective enzymatic deacylation as above.

Selective enzymatic acylation means that the enzymatic acylation is preferentially effective for conversion of one of the enantiomers of a compound of formula (II) preferentially leaving the other enantiomer of the compound of formula (II) unconverted in the reaction mixture.

Selective enzymatic deacylation means that the enzymatic deacylation is preferentially effective for conversion of one of the enantiomers of a compound of formula (IV), preferentially leaving the other enantiomer of the compound of formula (IV) unconverted in the reaction mixture.

The selective acylation according to the invention thus results in a mixture containing preferentially the compound of formula (II) in the S-form and the compound of formula (IV) in the R-form, or it may result in a mixture containing preferentially the compound of formula (II) in the R-form and the compound of formula (IV) in the S-form.

Likewise, the selective enzymatic deacylation may result in a mixture containing preferentially the compound of formula (IV) in the S-form and the compound of formula (II) in the R-form, or it may result in a mixture containing preferentially the compound of formula (IV) in the R-form and the compound of formula (II) in the S-form.

The composition mixture obtained after acylation or deacylation according to the invention depend on the specific hydrolase used and the conditions under which the reaction is carried out. Characteristic of the enzymatic acylation/deacylation according to the invention is that a considerably larger portion of one enantiomer is converted than of the other. The optical purity of the diol of formula (II) and/or the acylated compound of formula (IV) obtained by the optical resolution method of the present invention is usually at least 90% ee, preferably at least 95% ee, more preferably at least 97% ee and most preferably at least 98% ee. However, lower values for the optical purity are acceptable.

The starting material for the enzymatic method of the invention is a racemic diol of formula (II) or a racemic acyl derivative of formula (IV)

In a preferred embodiment of the invention R is halogen or cyano, most preferred cyano.

In a further preferred embodiment of the invention Hal is fluoro,

In a further embodiment of the invention, the dotted line in formula (II) and (IV) is a single bond.

In one embodiment Z is dimethylaminomethyl or a group that may be converted to dimethylaminomethyl. In a suitable embodiment Z is dimethylaminomethyl.

Most preferred, Hal is fluoro, R is cyano, the dotted line is a single bond and Z is dimethylaminomethyl.

The acylating agent used for the encymatic acylation according to the invention may suitable be one of the compounds of formula (IIIa), (IIIb) and (IIIc).

In another embodiment the acylating agent used according to the invention is any of the compounds of formula (IIIa) and (IIIb).

According to a further embodiment of the invention, the acylating agent used is a compound of formula (IIIa).

According to a still another embodiment of the invention, the acylating agent used is a compound of formula (IIIb).

According to another embodiment of the invention the acylating agent is a compound of formula (IIIc).

When the acylating agent is a compound of formula (IIIa), U is suitable O.

When the acylating agent is any of the above, W is suitable O.

When the acylating agent is any of the above, X is suitable O.

Suitable, the substituents $R^0$, $R^1$ and $R^2$ in any of the acylating agents (IIIa), (IIIb) and (IIIc) defined in any of the embodiments above are as follows:

$R^0$, $R^1$ and $R^2$ are independently selected from $C_{1-6}$-alkyl, $C_{2-6}$-alkenyl and $C_{2-6}$-alkynyl all of which may optionally be substituted one or more times with substituents selected from $C_{1-6}$-alkoxy, hydroxy, halogen, amino, nitro, cyano, $C_{1-6}$-alkylamino and di-($C_{1-6}$-alkyl)amino or $R^2$ is a suitable leaving group, such as succinimidyl, HOBt and pfp, or $R^0$ and $R^1$ together form a chain of 3-5 carbon atoms more suitable $R^0$, $R^1$ and $R^2$ are independently selected from $C_{1-4}$-alkyl, $C_{2-4}$-alkenyl and $C_{2-4}$-alkynyl all of which may optionally be substituted one or more times with substituents selected from $C_{1-4}$-alkoxy, $C_{1-4}$-alkylthio, hydroxy, halogen, amino, nitro, cyano, $C_{1-4}$-alkylamino and di-($C_{1-4}$-alkyl)amino or $R^2$ is a suitable leaving group, such as succinimidyl, HOBt and pfp or $R^0$ and $R^1$ together form a chain of 3-5 carbon atoms, more preferred $R^0$, $R^1$ and $R^2$ are independently selected from $C_{1-3}$-alkyl, $C_{2-3}$-alkenyl and $C_{2-3}$-alkynyl all of which may optionally be substituted one or more times with substituents selected from $C_{1-3}$-alkoxy, $C_{1-3}$-alkylthio, hydroxy, halogen, amino, nitro, cyano, $C_{1-3}$-alkylamino and di-($C_{1-3}$-alkyl)amino, even more preferred $R^0$ and $R^1$ is $C_{1-3}$-alkyl, in particular unbranched $C_{1-3}$-alkyl and $R^2$ is $C_{1-3}$-alkyl substituted one or more times with halogen or $R^2$ is $C_{2-3}$-alkenyl.

Suitably, the substituents $R^0$ and $R^1$ in acylating agents of formula (IIIa) as defined in any of the embodiments above, are as follows:

$R^0$ and $R^1$ are independently selected from $C_{1-6}$-alkyl, $C_{2-6}$-alkenyl and $C_{2-6}$-alkynyl all of which may optionally be substituted one or more times with substituents selected from $C_{1-6}$-alkoxy, $C_{1-6}$-alkylthio, hydroxy, halogen, amino, nitro, cyano, $C_{1-6}$-alkylamino and di-($C_{1-6}$-alkyl)amino, more suitable $R^0$ and $R^1$ are independently selected from $C_{1-4}$-alkyl, $C_{2-4}$-alkenyl and $C_{2-4}$-alkynyl all of which may optionally be substituted one or more times with substituents selected from $C_{1-4}$-alkoxy, $C_{1-4}$-alkylthio, hydroxy, halogen, amino, nitro, cyano, $C_{1-4}$-alkylamino and di-($C_{1-4}$-alkyl)amino, preferably $R^0$ and $R^1$ are independently selected from $C_{1-3}$-alkyl, $C_{2-3}$-alkenyl and $C_{2-3}$-alkynyl all of which may all optionally be substituted one or more times with substituents selected from $C_{1-3}$-alkoxy, $C_{1-3}$-alkylthio, hydroxy, halogen, amino, nitro, cyano, $C_{1-3}$-alkylamino and di-($C_{1-3}$-alkyl)amino, more preferred $R^0$ and $R^1$ are independently $C_{1-4}$-alkyl and most preferred, and most preferred $R^0$ and $R^1$ is $C_{1-3}$-alkyl, in particular unbranched $C_{1-3}$-alkyl, suitable propyl.

Suitably, the substituents $R^1$ and $R^2$ in acylating reagents of formula (IIIb) as defined in any of the embodiments above, are as follows:

$R^1$ and $R^2$ are independently selected from $C_{1-6}$-alkyl, $C_{2-6}$-alkenyl and $C_{2-6}$-alkynyl all of which may optionally be substituted one or more times with substituents selected from $C_{1-6}$-alkoxy, $C_{1-6}$-alkylthio, hydroxy, halogen, amino, nitro, cyano, $C_{1-6}$-alkylamino and di-($C_{1-6}$-alkyl)amino or $R^2$ is another leaving group, such as succinimidyl, HOBt and pfp, more suitable $R^1$ and $R^2$ are independently selected from $C_{1-4}$-alkyl, $C_{2-4}$-alkenyl and $C_{2-4}$-alkynyl all of which may optionally be substituted one or more times with substituents selected from $C_{1-4}$-alkoxy, $C_{1-4}$-alkylthio, hydroxy, halogen, amino, nitro, cyano, $C_{1-4}$-alkylamino and di-($C_{1-4}$-alkyl)amino or $R^2$ is another leaving group, such as succinimidyl, HOBt and pfp, preferably $R^1$ is selected from $C_{1-3}$-alkyl, $C_{2-3}$-alkenyl and $C_{2-3}$-alkynyl all of which may optionally be substituted one or more times with substituents selected from $C_{1-3}$-alkoxy, $C_{1-3}$-alkylthio, hydroxy, halogen, amino, nitro, cyano, $C_{1-3}$-alkylamino and di-($C_{1-3}$-alkylamino and $R^2$ is $C_{1-4}$-alkyl substituted one or more times with halogen, $R^2$ is $C_{2-4}$-alkenyl or $R^2$ is another leaving group, such as succinimidyl, HOBt and pfp, more preferred $R^1$ is $C_{1-3}$-alkyl, $C_{2-3}$-alkenyl or $C_{2-3}$-alkynyl all of which may optionally be substituted one or more times with substituents selected from $C_{1-3}$-alkoxy, $C_{1-3}$-alkylthio, hydroxy, halogen, amino, nitro, cyano, $C_{1-3}$-alkylamino and di-($C_{1-3}$-alkylamino and $R^2$ is $C_{1-3}$-alkyl substituted one or more times with halogen or $R^2$ is $C_{2-3}$-alkenyl, still more preferred $R^1$ is $C_{1-3}$-alkyl and $R^2$ is $C_{1-3}$-alkyl substituted one or more times with halogen or $R^2$ is $C_{2-3}$-alkenyl, and more suitable $R^1$ is $C_{1-3}$-alkyl, in particular unbranched $C_{1-3}$-alkyl, such as methyl, ethyl or propyl and $R^2$ is $C_{2-3}$-alkenyl.

$R^2$ meaning $C_{1-3}$-alkyl substituted one or more times with halogen is a suitable leaving group including groups such as 2,2,2-trichloroethyl and 2,2,2-trifluoroethyl, in particular 2,2,2-trifluoroethyl.

In a specific embodiment of the invention, the acylating agent of formula (IIIb) as above is a compound wherein $R^2$ is vinyl.

According to another specific embodiment of the invention, the acylating agent of formula (IIIb) is a compound as above wherein $R^1$ is propyl. This specific embodiment covers a preferred acylating agent of the invention, namely vinyl butyrate.

According to a further embodiment of the invention, the acylating agent is a compound of formula (IIIc).

Suitably, the substituent $R^1$ in the compound of formula (IIIc) as defined in any of the embodiments above, are as follows:

$R^1$ is $C_{1-6}$-alkyl, $C_{2-6}$-alkenyl and $C_{2-6}$-alkynyl all of which may optionally be substituted one or more times with substituents selected from $C_{1-6}$-alkoxy, $C_{1-6}$-alkylthio, hydroxy, halogen, amino, nitro, cyano, $C_{1-4}$-alkylamino and di-($C_{1-6}$-alkyl)amino, more suitable $R^1$ is $C_{1-4}$-alkyl, $C_{2-4}$-alkenyl and $C_{2-4}$-alkynyl all of which may optionally be substituted one or more times with substituents selected from $C_{1-4}$-alkoxy, $C_{1-4}$-alkylthio, hydroxy, halogen, amino, nitro, cyano, $C_{1-4}$-alkylamino and di-($C_{1-4}$-alkylamino, preferably $R^1$ is $C_{1-3}$-alkyl, $C_{2-3}$-alkenyl and $C_{2-3}$-alkynyl all of which may optionally be substituted one or more times with $C_{1-3}$-alkoxy, $C_{1-3}$-alkylthio, hydroxy, halogen, amino, nitro, cyano, $C_{1-3}$-alkylamino and di-($C_{1-3}$-alkyl)amino, more preferred $R^1$ is $C_{1-3}$-alkyl, $C_{2-3}$-alkenyl or $C_{2-3}$-alkynyl, and more suitable suitable $R^1$ is $C_{1-3}$-alkyl, in particular unbranched $C_{1-3}$-alkyl, such as methyl, ethyl or propyl.

V is suitable chloro.

The acylating agent used according to the invention may also be an isocyanate of formula $R^1$—N=C=O or an isothiocyanate of the formula $R^1$—N=C=S.

Thus, in a further embodiment of the invention, the acylating agent is an isothiocyanate of the formula $R^1$—N=C=O.

According to another embodiment of the invention, the acylating agent is an isocyanate of formula $R^1$—N=C=S.

Suitably, the substituent $R^1$ in the isocyanate and the isothiocyanate as defined in any of the embodiments above, are as follows:

$R^1$ is $C_{1-6}$-alkyl, $C_{2-6}$-alkenyl or $C_{2-6}$-alkynyl all of which may optionally be substituted one or more times with substituents selected from $C_{1-6}$-alkoxy, $C_{1-6}$-alkylthio, hydroxy, halogen, amino, nitro, cyano, $C_{1-4}$-alkylamino and di-($C_{1-6}$-alkyl)amino, more suitable $R^1$ is $C_{1-4}$-alkyl, $C_{2-4}$-alkenyl or $C_{2-4}$-alkynyl all of which may optionally be substituted one or more times with substituents selected from $C_{1-4}$-alkoxy, $C_{1-4}$-alkylthio, hydroxy, halogen, amino, nitro, cyano, $C_{1-4}$-alkylamino and di-($C_{1-4}$-alkyl)amino, preferably $R^1$ is $C_{1-3}$-alkyl, $C_{2-3}$-alkenyl or $C_{2-3}$-alkynyl all of which may optionally be substituted one or more times with $C_{1-3}$-alkoxy, $C_{1-3}$-alkylthio, hydroxy, halogen, amino, nitro, cyano, $C_{1-3}$-alkylamino and di-($C_{1-3}$-alkylamino, more preferred $R^1$ is $C_{1-3}$-alkyl, $C_{2-3}$-alkenyl or $C_{2-3}$-alkynyl, and more suitable $R^1$ is $C_{1-3}$-alkyl, in particular unbranched $C_{1-3}$-alkyl, such as methyl, ethyl or propyl The invention also covers a method for selective enzymatic deacylation of a racemic compound of formula (IV) as defined above.

Suitable, the racemic compound of formula (IV) used, is a compound wherein Y is O, or S.

According to a further embodiment the racemic compound of formula (IV) used, is a compound wherein Y is O.

In still another embodiment of the invention the racemic compound of formula (IV) used is a compound wherein Y is S.

In another embodiment of the invention the racemic compound of formula (IV) used is a compound wherein Y is a bond.

Suitably, the substituent $R^1$ in the racemic compound (IV) as defined in any of the embodiments above, is as follows: $C_{1-10}$-alkyl, $C_{2-10}$-alkenyl or $C_{2-10}$-alkynyl all of which may optionally be substituted one or more times with substituents selected from $C_{1-10}$-alkoxy, $C_{1-10}$-alkylthio, hydroxy, halogen, amino, nitro, cyano, $C_{1-10}$-alkylamino and di-($C_{1-10}$-alkyl)amino, more suitable $R^1$ is $C_{1-10}$-alkyl, $C_{2-10}$-alkenyl or $C_{2-10}$-alkynyl all of which may optionally be substituted one or more times with substituents selected from hydroxy, halogen, amino, nitro and cyano, preferably $R^1$ is $C_{1-10}$alkyl, preferably unbranched $C_{1-10}$alkyl and more preferred $R^1$ is unbranched $C_{4-10}$-alkyl.

According to the invention, selective enzymatic acylation is carried out under conditions substantially suppressing hydrolysis. Hydrolysis, which is the reverse reaction of the acylation reaction, takes place if water is present in the reaction system.

Thus, selective enzymatic acylation is preferably carried out in a water-free organic solvent or almost anhydrous organic solvent (enzymes normally require the presence of some water to be active). The examples below, illustrate how addition of water affects conversion. The percentage of water allowed in a particular reaction system, may be determined by a person skilled in the art.

The organic solvent which may be used for the acylation reaction, is not particularly important as long as it does not deactivate the enzyme used. Suitable solvents include hydrocarbons such as hexane, heptane, benzene and toluene; ethers such as diethyl ether, diisopropyl ether, tetrahydrofuran, 1,4-dioxane, tert-butyl methyl ether and dimethoxyethane; ketones such as acetone, diethyl ketone, butanon, and methyl ethyl ketone; esters such as methyl acetate, ethyl acetate, ethyl butyrate, vinyl butyrate and ethyl benzoate; halogenated hydrocarbons such as methylene chloride, chloroform and 1,1,1-trichloroethane; secondary and tertiary alcohols, such as tert-butanol; nitrogen-containing solvents such as dimethylformamide, acetoamide, formamide, acetonitrile and propionitrile; and aprotic polar solvents such as dimethylsulfoxide, N-methylpyrrolidone and hexamethylphosphorous triamide.

Among them, hydrocarbons such as hexane, heptane, benzene and toluene, ethers such as diethyl ether, diisopropyl ether, 1,4-dioxane and tert-butyl methyl ether and esters such as vinyl butyrate, are preferred. For one enzymes the most preferred solvents may be aromatic hydrocarbons such as benzene or toluene and ethers, most preferred toluene and for another enzyme the most preferred solvents may be ethers such as 1,4-dioxane (see the examples below). The above solvents may be used singly or in a combination of two or more solvents.

The concentration of racemic diol of formula (II) and acylating agent should not be too high as a high concentration of reagents in the solvent may lead to non-selective acylation of the racemic diol. Suitable the concentration of racemic diol and acylating reagent is each below 1.0 M, more suitable below 0.5 M, even more suitable below 0.2 M or even more suitable below 0.1 M. A person skilled in the art will be able to determine the optimal concentration of racemic diol and acylating agent.

Selective enzymatic deacylation is preferably carried out in water or a mixture of water and an organic solvent, suitable in presence of a buffer. The organic solvent which may be used in the reaction, is not particularly important as long as it does not deactivate the enzyme used. Suitable organic solvents are solvents miscible with water such as alcohols, acetonitrile, DMF, DMSO, dioxane, DME and diglyme. The skilled person will be able to identify other suitable solvents. A person skilled in the art will be able to determine the optimal concentration of racemic compound of formula (IV) used in the reaction The stereoselectivity of the enzyme used, may be increased by carrying out the acylation or deacylation in presence of an organic acid and/or an organic base.

Accordingly, the present invention also relates to a process wherein the enzymatic acylation or the enzymatic deacylation is carried out in presence of an organic base or an organic acid or a mixture thereof.

In a particular embodiment, the invention relates to a process wherein the enzymatic acylation or enzymatic deacylation is carried out in the presence of an organic acid, suitable an organic carboxylic acid.

In a further embodiment, the enzymatic acylation is carried out in presence of an organic acid, suitable an organic carboxylic acid.

Suitable the above mentioned organic acid is an aromatic carboxylic acid or an aliphatic carboxylic acid.

As an organic acid which may be used in the reaction, there may be mentioned, alkyl carboxylic acids, cycloalkylcarboxylic acids, cycloalkylalkylcarboxylic acids, optionally substituted phenyl-alkylcarboxylic acids and optionally substituted phenylcarboxylic acids. Suitable aliphatic carboxylic acids, are carboxylic acids such as formic acid, acetic acid, propionic acid, n-butyric acid, iso-butyric acid, 2-ethylbutyric acid, n-valeric acid, iso-valeric acid, pivalic acid, n-caproic acid, iso-caproic acid, decanoic acid, crotonic acid, palmitic acid, cyclopentanecarboxylic acid, cyclohexanecarboxylic acid, phenyl-$C_{1-4}$-alkylcarboxylic acids such as 3-phenylpropionic acid, 4-phenylbutyric acid, oxalic acid, malonic acid and tartaric acid. Suitable aromatic carboxylic acids, includes acids such as benzoic acid, p-chlorobenzoic acid, p-nitrobenzoic acid, p-methoxybenzoic acid, p-toluic acid, o-toluic acid, m-toluic acid, naphthoic acid, phthalic acid and terephthalic acid, salicylic acid, hydrocinnamic acid for instance.

Thus, according to one embodiment of the invention, the organic acid used to improve stereoselectivity of the enzyme is selected from n-propionic acid, iso-propionic acid, n-butyric acid, iso-butyric acid, iso-valeric acid, 2-ethylbutyric acid, crotonic acid, palmitic acid, cyclohexanecarboxylic acid, pivalic acid, benzoic acid and p-toluic acid, salicylic acid and 3-phenylpropionic acid. According to a further embodiment of the invention, the carboxylic acid used is pivalic acid.

The amount of the organic acid to be used is not particularly restricted, but the molar ratio relative to a substrate is usually 0.1 to 10, preferably 1.0 to 3.0, and more preferably 1.0 to 2.0.

Alternatively, a tertiary amine may be used to improve selectivity of the enzyme, either alone or together with any of the above mentioned organic acid. As suitable organic base there may be mentioned, triethyl amine, pyridine, 4-dimethylaminopyridine and pyridine is preferred. Suitable combinations of organic acid and organic base are benzoic acid and pyridine for example.

The amount of the tertiary amine to be used is not particularly restricted, but the molar ratio relative to a substrate is usually 0.5 to 3.0, and preferably 0.5 to 2.0.

The enzymatic acylation or deacylation according to the invention is carried out using a hydrolase, such as a lipase, an esterase, an acylase or a protease.

Thus, according to one embodiment of the invention, enzymatic acylation is performed with a hydrolase, such as a lipase, an esterase, an acylase or a protease. The enzymes useful according to the invention are such enzymes capable of performing R-selective acylation or S-selective acylation of the primary hydroxy group in the racemic compound of formula (II).

According to another embodiment of the invention, enzymatic deacylation is performed with a hydrolase, such as a lipase, an esterase, an acylase or a protease. The enzymes useful according to the invention are such enzymes capable of performing R-selective deacylation or S-selective deacylation of the acyl group in the racemic compound of formula (IV).

As used herein "hydrolase" and "enzyme" either generally or in relation to a specific enzyme, means not only the enzyme itself, but also cultured products containing the enzyme, such as culture fluid containing a cell body, or a cultured cell body, and processed product of the cultured product (for example a crude extract, a freeze-dried microorganism or cell, an acetone dried microorganism or cell, a ground product of such microorganism or cell, or the like).

Additionally, the "enzyme" or "hydrolase" may be immobilized as the enzyme itself or as a cell body by known techniques, and may be used in immobilized form. The immobilization may be carried out by methods known to the person skilled in the art, such methods include, for example carrier bonding, cross linking, encapsulation and the like.

Thus, in one embodiment of the invention the hydrolase is used in the form of an immobilized enzyme or Cross-Linked Enzyme Crystal (CLEC) enzymes.

It has been found that enzymatic acylation according to the invention may be carried out using Novozyme 435, from *Candida antartica*, LipoZyme TL IM from *Thermomyces lanuginosus* or Lipoprotein Lipase *pseudomonas* sp. (isolated from *Pseudomonas Cepacia* and obtained from Fluka), and particularly good results have been found when using Novozyme 435, from *Candida antartica* or Lipoprotein Lipase *pseudomonas* sp.

Thus, according to one embodiment of the invention, the enzyme used is *Pseudomonas* sp. lipoprotein lipase, *Candida antartica* lipase B or *Thermomyces lanuginosus* lipase.

According to another embodiment of the invention, the enzyme used is *Pseudomonas* sp. lipoprotein lipase or *Candida antartica* lipase B.

As mentioned above, use of one of the above mentioned enzymes according to the invention also covers the use of cultured products containing the enzyme, such as culture fluid containing a cell body, or a cultured cell body, processed product of the cultured product and any immobilized forms of these enzymes/cultured products.

The use of any of the above specifically mentioned enzymes according to the invention also covers the use of mutants, variants or any equivalents of the above specifically mentioned enzymes, which are capable of performing the selective acylation or deacylation according to the invention. The variants or equivalents thereof may be isolated from various strains of *Pseudomonas, Candida* or *Thermomyces*, or any other source, or they may be prepared by mutation of the DNA encoding the above mentioned enzymes leading to variations in the amino acid composition of the enzyme. Suitable the mutants or variants of the above mentioned enzymes are variants and mutants where single amino acids have been removed or replaced by other amino acids, and suitable the amino acid sequence of the variant or mutant is more than 60% identical, preferably more than 80% or most preferred more than 90% identical to the above mentioned enzymes.

Thus, according to one embodiment of the invention, the enzyme used is *Pseudomonas* sp. lipoprotein lipase or a mutant or variant thereof. Preferably *Pseudomonas* sp. lipoprotein lipase is used.

According to another embodiment of the invention, the enzyme used is *Candida antartica* lipase B or a mutant or variant thereof. Preferably, the enzyme used is *Candida antartica* lipase B.

According to a further embodiment of the invention the enzyme is Novozyme®435 (*Candida antartica* lipase B immobilized on acrylic resin, available from the company Novozymes A/S).

According to still another embodiment of the invention, the enzyme used is *Thermomyces lanuginosus* lipase or a mutant or variant thereof. Preferably the enzyme used is *Thermomyces lanuginosus* lipase.

According to a further embodiment of the invention, the enzyme used is Lipozyme™ TL IM, also available from the company Novozymes A/S.

The preferred reaction conditions for enzymatic acylation/deacylation differ depending on the particular enzyme used, whether it is immobilised or not etc.

A suitable temperature for the reaction lies between 0-80° C., more preferably between 20-60° C., or more preferred between 30-50° C.

The amount of enzyme to be used is not particularly restricted, but is usually 0.01-1.0, preferably 0.02-0.5 and more preferably 0.02-0.3, as weight ratio relative to substrate.

The reaction may be carried as a batch process or it may be carried out as a continuous process. The enzyme may be used in a plurality of batches repeatedly or continuously. The reaction time is not particularly restricted, and will depend on the enzyme used and the scale and type production method (batch or continuos).

The present invention also relates to an S- or R-enantiomer of a compound having the formula (IV)

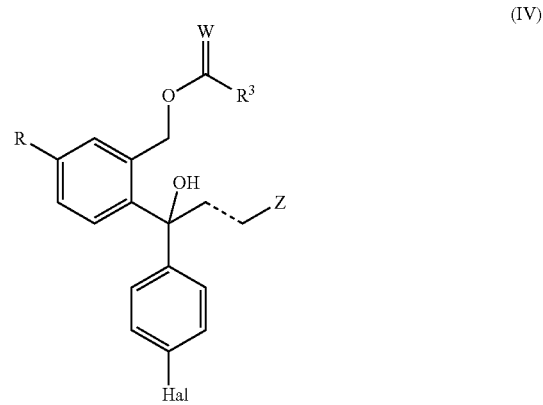

(IV)

wherein R, Hal, $R^3$, W, the dotted line and Z are as defined above, or a salt thereof.

According to one embodiment of the invention, the optically active acyl derivative above is the S-enantiomer. According to another embodiment of the invention, the optically active acyl derivative above is the R-enantiomer.

According to one embodiment of the invention the R- or S-enantiomer above is a compound wherein R is halogen or cyano, preferably R is cyano.

According to a further embodiment of the invention, the R- or S-enantiomer above is a compound wherein Hal is fluoro.

According to a further embodiment of the invention, the R- or S-enantiomer above is a compound wherein the dotted line represents a single bond.

In another embodiment of the invention, the R- or S-enantiomer above is a compound wherein Z is dimethylaminomethyl or a group that may be converted to dimethylaminomethyl, more suitable Z is dimethylaminomethyl, and the other substituents are as defined above.

In another embodiment of the invention, the R- or S-enantiomer above is a compound wherein Z is dimethylaminomethyl, Hal is fluoro, the dotted line represents a single bond, and R is cyano or halogen, suitable cyano.

In a further embodiment of the invention, the R- or S-enantiomer above is a compound wherein Y is O, or S, preferably Y is O and the other substituents are as defined above. In a further embodiment of the invention, the R- or S-enantiomer above is a compound wherein Y is S and the other substituents are as defined above.

In a further embodiment of the invention, the R- or S-enantiomer above is a compound wherein Y is a bond and the other substituents are as defined above.

In a further embodiment of the invention, the R- or S-enantiomer above is a compound wherein Y is NH and the other substituents are as defined above.

Suitable, the R- or S-enantiomer as defined in any of the embodiments above is a compound wherein $R^1$ is $C_{1-6}$-alkyl, $C_{2-6}$-alkenyl or $C_{2-6}$-alkynyl all of which may optionally be substituted one or more times with substituents selected from $C_{1-6}$-alkoxy, $C_{1-6}$-alkylthio, hydroxy, halogen, amino, nitro, cyano, $C_{1-6}$-alkylamino and di-($C_{1-6}$-alkyl)amino, more suitable $R^1$ is $C_{1-4}$-alkyl, $C_{2-4}$-alkenyl or $C_{2-4}$-alkynyl all of which may optionally be substituted one or more times with substituents selected from $C_{1-4}$-alkoxy, $C_{1-4}$-alkylthio, hydroxy, halogen, amino, nitro, cyano, $C_{1-4}$-alkylamino and di-($C_{1-4}$-alkyl)amino, preferably $R^1$ is $C_{1-3}$-alkyl, $C_{2-3}$-alkenyl or $C_{2-3}$-alkynyl all of which may optionally be substituted one or more times with substituents selected from $C_{1-3}$-alkoxy, $C_{1-3}$-alkylthio, hydroxy, halogen, amino, nitro, cyano, $C_{1-3}$-alkylamino and di-($C_{1-3}$-alkyl)amino and most preferred $R^1$ is $C_{1-3}$-alkyl, in particular unbranched $C_{1-3}$-alkyl.

According to another suitable embodiment of the invention, the R- or S-enantiomer as defined in any of the embodiments above is a compound wherein $R^1$ is as follows: $C_{1-10}$-alkyl, $C_{2-10}$-alkenyl or $C_{2-10}$-alkynyl all of which may optionally be substituted one or more times with substituents selected from $C_{1-10}$-alkoxy, $C_{1-10}$-alkylthio, hydroxy, halogen, amino, nitro, cyano, $C_{1-6}$-alkylamino and di-($C_{1-10}$-alkyl)amino, more suitable $R^1$ is $C_{1-10}$-alkyl, $C_{2-10}$-alkenyl or $C_{2-10}$-alkynyl all of which may optionally be substituted one or more times with substituents selected from hydroxy, halogen, amino, nitro and cyano, preferably $R^1$ is $C_{1-10}$-alkyl, preferably unbranched $C_{1-10}$-alkyl and more preferred $R^1$ is unbranched $C_{4-10}$.

After the completion of the acylation reaction or the deacylation reaction, an enantiomer of the diol derivative represented by the formula (II) is obtained as a mixture with the opposite enantiomer of the compound of formula (IV). This reaction mixture is then optionally separated from the enzyme.

In order to obtain the desired enantiomer of formula (II) and/or (IV) with high chemical purity, it is necessary to separate it form the opposite enantiomer of formula (IV) and (II), respectively, in an efficient manner. However, it is difficult to efficiently separate the enantiomers by generally known methods because the structure of the acyl derivative of formula (IV) is so similar to the structure of the diol of formula (II).

The present inventors have made intensive investigations and have as a result found that the enantiomer of a compound of formula (II) in the form of a salt with an acid is efficiently distributed into an aqueous layer and the opposite enantiomer of a compound of formula (IV) in the form of a salt with the acid is efficiently distributed into an organic layer when the reaction mixture is treated with a mixed solvent containing organic solvent and water in the presence of an acid.

Thus, according to another embodiment, the invention relates to a method for the isolation and purification of an acyl derivative having the formula

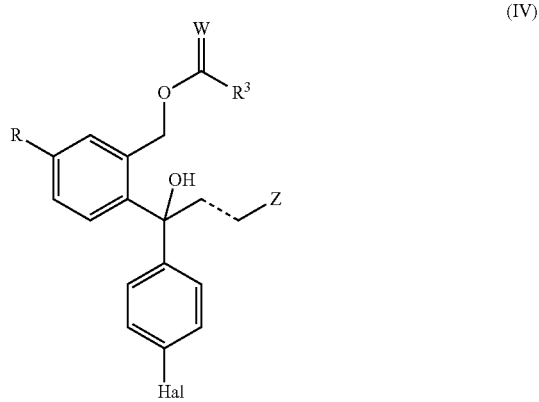

(IV)

wherein R is cyano or a group which may be converted to a cyano group, Hal is halogen, the dotted line is a double or a single bond and Z is a group —$CH_2$—N(R'R'') wherein R' and $C_{1-6}$-alkyl, or R' and R'' are connected to each other to form a cyclic structure including the N-atom to which they are attached, or Z is a group which may be converted to a dimethylaminomethyl group, W is O or S and $R^3$ is —Y—$R^1$ wherein Y is a bond, O, S or NH and $R^1$ is $C_{1-10}$-alkyl, $C_{2-10}$-alkenyl or $C_{2-10}$-alkynyl all of which may optionally be substituted with one or more substituents selected from $C_{1-10}$-alkoxy, $C_{1-10}$-alkylthio, hydroxy, halogen, amino, nitro, cyano, $C_{1-10}$-alkylamino, di-($C_{1-10}$-alkyl)amino, aryl, aryloxy, arylthio and heteroaryl, or $R^1$ is aryl, wherein any of the the aryl and heteroaryl groups may optionally be substituted one or more times with substituents selected from $C_{1-10}$-alkyl, $C_{2-10}$-alkenyl, $C_{2-10}$-alkynyl, $C_{1-10}$-alkoxy, $C_{1-10}$-alkylthio, hydroxy, halogen, amino, nitro, cyano, $C_{1-10}$-alkylamino and di-($C_{1-10}$-alkyl)amino, or a salt thereof and/or a diol of formula

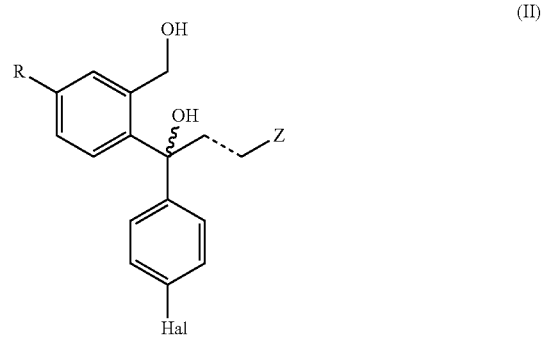

(II)

wherein R, Hal, the dotted line and Z are as defined above, or a salt thereof, from a mixture containing a compound of formula (IV) and a diol of formula (II), which comprises:

a) treating said mixture containing the acyl of formula (IV) and the diol of formula (II) in a mixture of water and an organic solvent in the presence of an acid;

b) separating the aqueous phase containing the diol of formula (II) as a salt of said acid from the organic phase to obtain an organic phase containing the acyl derivative of formula (IV) as a salt of said acid;

optionally isolating the compound of formula (II) as the base or as a salt thereof and optionally the compound of formula (IV) as the base or as a salt thereof.

According to one embodiment of the invention R is halogen or cyano, preferably cyano in the method for isolation and purification above.

According to another embodiment of the invention Hal is fluoro in the method for isolation and purification above.

According to a preferred embodiment, the dotted line represents a single bond.

In another embodiment of the invention, Z is dimethylaminomethyl or a group that may be converted to a dimethylaminomethyl group. Suitable Z is dimethylaminomethyl.

According to a preferred embodiment of the invention Hal is fluoro, Z is dimethylaminomethyl, the dotted line is a single bond and R is cyano or halogen, preferably cyano.

In a further embodiment of the invention the compound of formula (IV) in the method for isolation and purification above, is a compound wherein Y is O, or S, preferably Y is O and the other substituents are as defined above. In a further embodiment of the invention the compound of formula (IV) in the method for isolation and purification above, is a compound wherein Y is S.

In a further embodiment of the invention the compound of formula (IV) in the method for isolation and purification above, is a compound wherein Y is a bond and the other substituents are as defined above.

In a further embodiment of the invention the compound of formula (IV) in the method for isolation and purification above, is a compound wherein Y is NH and the other substituents are as defined above.

In a preferred embodiment of the invention, the compound of formula (IV) in the method for isolation and purification above, is a compound wherein $R^1$ is $C_{1-6}$-alkyl, $C_{2-6}$-alkenyl or $C_{2-6}$-alkynyl all of which may optionally be substituted one or more times with substituents selected from $C_{1-6}$-alkoxy, $C_{1-6}$-alkylthio, hydroxy, halogen, amino, nitro, cyano, $C_{1-6}$-alkylamino and di-($C_{1-6}$-alkyl)amino, more preferred $R^1$ is $C_{1-4}$-alkyl, $C_{2-4}$-alkenyl or $C_{2-4}$-alkynyl all of which may optionally be substituted one or more times with substituents selected from $C_{1-4}$-alkoxy, $C_{1-4}$-alkylthio, hydroxy, halogen, amino, nitro, cyano, $C_{1-4}$-alkylamino and di-($C_{1-4}$-alkyl)amino, preferably $R^1$ is $C_{1-3}$-alkyl, $C_{2-3}$-alkenyl and $C_{2-3}$-alkynyl all of which may optionally be substituted one or more times with substituents selected from $C_{1-3}$-alkoxy, $C_{1-3}$-alkylthio, halogen, amino, nitro, cyano, $C_{1-3}$-alkylamino and di-($C_{1-3}$-alkyl)amino and most preferred $R^1$ is $C_{1-3}$-alkyl, in particular unbranched $C_{1-3}$-alkyl.

In another preferred embodiment of the invention, the compound of formula (IV) in the method for isolation and purification above, is a compound wherein $R^1$ is as follows: $C_{1-10}$-alkyl, $C_{2-10}$-alkenyl or $C_{2-10}$-alkynyl all of which may optionally be substituted one or more times with substituents selected from $C_{1-10}$-alkoxy, $C_{1-10}$-alkylthio, hydroxy, halogen, amino, nitro, cyano, $C_{1-6}$-alkylamino and di-($C_{1-10}$-alkyl)amino, more suitable $R^1$ is $C_{1-10}$-alkyl, $C_{2-10}$-alkenyl or $C_{2-10}$-alkynyl all of which may optionally be substituted one or more times with substituents selected from hydroxy, halogen, amino, nitro and cyano, preferably $R^1$ is $C_{1-10}$-alkyl, preferably unbranched $C_{1-10}$-alkyl and more preferred $R^1$ is unbranched By the above method for isolation and purification, a salt of the R- or S-enantiomer of a compound having the formula (II) with an acid may be selectively extracted into an aqueous layer and a salt of the opposite enantiomer of a compound of formula (IV) with an acid may be selectively separated into an organic layer by treating, in the presence of the acid, a mixture comprising an enantiomer of formula (II) and the opposite enantiomer of formula (IV), reaction solvent and the like with an organic solvent and water, and in presence of an acid. In this case, the salt of the enantiomer of formula (IV) and the salt of the enantiomer of formula (II) may be separated with little loss of the desired enantiomers.

According to one embodiment of the above method for isolation and purification, the S-enantiomer of the compound of formula (IV) is isolated from the R-enantiomer of the compound of formula (II).

According to another embodiment of the above method for isolation and purification, the S-enantiomer of the diol of formula (II) is isolated from the R-enantiomer of the acyl derivative of formula (IV).

The amount of water to be used is 1:2 to 1:100, preferably 1:5 to 1:50, as a ratio between the compound of formula (II) and water. In addition, prior to the extraction with water, the reaction solvent may be evaporated to reduce the amount thereof or may be substituted with another organic solvent.

The acid which may be used in the above isolation and purification process is not particularly restricted, but for example, there may be mentioned, mineral acids such as hydrochloric acid, sulfuric acid and phosphoric acid; organic acids, in particular carboxylic acids, represented by aliphatic carboxylic acids such as formic acid, acetic acid, propionic acid, n-butyric acid, iso-butyric acid, n-valeric acid, iso-valeric acid, pivalic acid, n-caproic acid, iso-caproic acid, cyclopentanecarboxylic acid, cyclohexanecarboxylic acid, oxalic acid, malonic acid and tartaric acid; or aromatic carboxylic acids such as benzoic acid, p-chlorobenzoic acid, p-nitrobenzoic acid, p-methoxybenzoic acid, p-toluic acid, o-toluic acid, m-toluic acid, naphthoic acid, phthalic acid and telephtalic acid. Among them, organic acids are preferred, in particular carboxylic acids such as n-butyrate, iso-valerate, cyclohexanecarboxylic acid, pivalic acid, benzoic acid and o-toluic acid, and particularly preferred is pivalic acid. Needless to say, the above acids may be used singly or in a combination of two or more species. The amount of the acids to be used is not particularly restricted, but the molar ratio of the sum of the compounds of formula (IV) and (II) and acid, is usually 1:1 to 1:5, and preferably 1:1 to 1:3.

The acid used in the present isolation and purification step may be the same as the organic acid used in the acylation or deacylation reaction according to the invention or may be a different one.

As an organic solvent which may be used in the isolation and purification step, there may be mentioned, for example, hydrocarbons such as hexane, heptane, benzene and toluene; ethers such as diethyl ether, tetrahydrofuran, 1,4-dioxane, tert-butyl methyl ether and dimethoxyethane; ketones such as acetone, diethyl ketone and methyl ethyl ketone; esters such as methyl acetate, ethyl acetate, ethyl butyrate and ethyl benzoate; halogenated hydrocarbons such as methylene chloride, chloroform and 1,1,1-trichloroethane. Among them, aliphatic hydrocarbons, such as hexane and heptane and aromatic hyderocarbons, such as benzene and toluene are preferred. Most preferred are aromatic hydrocarbons and most preferred is toluene. The above solvents may be used singly or in a combination of two or more solvents.

Temperature of the isolation and purification step is preferably at 0 to 80° C., and more preferably at 10 to 40° C. and most preferred at 20 to 30° C.

Following, separation of the salts of the compounds of formula (II) and (IV) according to the above method for isolation and purification, minor amounts of the compound of formula (IV) which is partly mixed in an aqueous layer of the salt of the compound of formula (II) with an acid, and the like can be efficiently removed by washing the aqueous layer with an organic solvent.

The salt of the diol of formula (II) may be used as an aqueous solution of the salt, and if needed, it may be used as a solution in another solvent or a concentrate obtained by concentration, solvent substitution or the like operation. Furthermore, it can be used as a crystal obtained by crystallization or the like operation. However, it is usual that the diol of formula (II) is be used as a free diol form obtained by the following operations: A mixture containing the diol of formula (II) and an organic solvent and/or its concentrate is obtained by treating an aqueous layer with a general base such as sodium hydroxide or potassium hydroxide to control the pH of the aqueous layer to be at least 9, preferably at least 11, then extracting the free amine form of the diol of formula (II) with an organic solvent, followed by washing and concentrating the extract. The chemical purity of the diol of formula (II) obtained by the series of isolation and purification method is usually at least 95%, preferably at least 97%, more preferably at least 99% and most preferably at least 99.5%.

On the other hand, the compound of formula (IV) obtained by the above operations may be washed with an aqueous phase in order to improve chemical purity of the product. The compound of formula (IV) may be obtained as a free amine form by treating the ammonium salt of the compound of formula (IV), obtained by the above operations, with a base. The chemical purity of the diol of formula (IV) obtained by the series of isolation and purification method is usually at least 95%, preferably at least 97%, more preferably at least 99% and most preferably at least 99.5%.

The optical purity of the product obtained after separation of the enantiomers of formula (II) and (IV) as above, may be improved before further processing. Improvement of the optical purity may be obtained by chromatography as described in WO 03/011278 or by crystallisation of diastereomeric esters or salts with optically active acids as described in U.S. Pat. No. 4,943,590.

According to a further embodiment of the invention, the mixture of compound of formula (II) and compound of formula (IV) which is separated by the above method for isolation and purification has been prepared by the selective acylation and in another embodiment by selective deacylation according to the invention.

The invention also relates to another novel method for the separation of the R- or S-diol of formula (II) from the acyl derivative of formula (IV) of the other enantiomer whereby the desired compound may be isolated and purified.

According to this other method for isolation and purification the acyl derivative having the formula

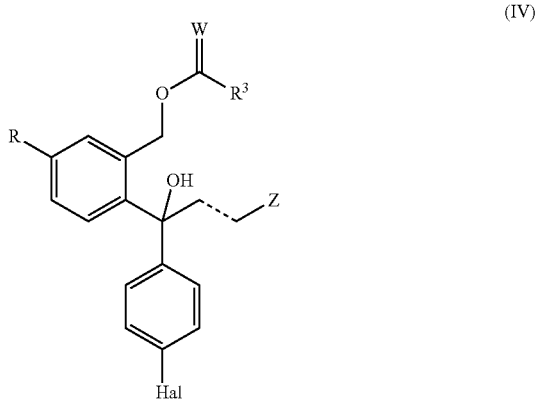

(IV)

wherein R is cyano or a group which may be converted to a cyano group, Hal is halogen, the dotted line represents a double or a single bond, Z is a group) —CH$_2$—N(R'R") wherein R' and R" are C$_{1-6}$-alkyl, or R' and R" are connected to each other to form a cyclic structure including the N-atom to which they are attached, or Z is a group which may be converted to a dimethylaminomethyl group, W is O or S; and R$^3$ is —Y—R$^1$ wherein Y is a bond, O, S or NH and R$^1$ is C$_{1-10}$-alkyl, C$_{2-10}$-alkenyl or C$_{2-10}$-alkynyl all of which may optionally be substituted one or more times with substituents selected from C$_{1-10}$-alkoxy, C$_{1-10}$-alkylthio, hydroxy, halogen, amino, nitro, cyano, C$_{1-10}$-alkylamino, di-(C$_{1-10}$-alkyl)amino, aryl, aryloxy, arylthio and heteroaryl, or R$^1$ is aryl, wherein any of the the aryl and heteroaryl groups may optionally be substituted one or more times with substituents selected from C$_{1-10}$-alkyl, C$_{2-10}$-alkenyl, C$_{2-10}$-alkynyl, C$_{1-10}$alkoxy, C$_{1-10}$-alkylthio, hydroxy, halogen, amino, nitro, cyano, C$_{1-10}$-alkylamino and di-(C$_{1-10}$-alkyl)amino, or a salt thereof and/or the diol of formula

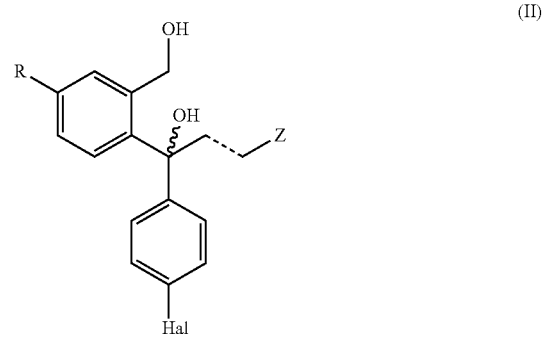

(II)

wherein R, Hal, the dotted line and Z are as defined above, or a salt thereof, iso isolated from a mixture containing a compound of formula (IV) and a compound of formula (II), by a method comprising:

a) treating said mixture containing the compound of formula (IV) and the diol of formula (II) in a mixture of water, a protic organic solvent and an apolar organic solvent;

b) separating the aqueous phase containing the diol of formula (II), from the organic phase to obtain an organic phase containing the compound of formula (IV);

optionally isolating the diol of formula (II) and/or (IV) as a base and optionally conversion of the compound of formula (II) and/or (IV) to a salt thereof.

Any of the above isolated phases (aqueous and organic) may additionally be washed one or more times with an organic or an aqueous solvent, respectively to improve the chemical purity of the product.

According to one embodiment of the above method for isolation and purification, the S-diol of the compound of formula (II) is separated from the R-enantiomer of the compound of formula (IV).

According to another embodiment of the above method for isolation and purification, the S-enantiomer of the compound of formula (IV) is separated from the R-enantiomer of the compound of formula (II).

According to one embodiment of the invention R is halogen or cyano, preferably cyano in the method for isolation and purification above.

According to another embodiment of the invention Hal is fluoro in the method for isolation and purification above.

According to a preferred embodiment, the dotted line represents a single bond.

In another embodiment of the invention, Z is dimethylaminomethyl or a group that may be converted to a dimethylaminomethyl group. Suitable Z is dimethylaminomethyl.

According to a preferred embodiment of the invention Hal is fluoro, Z is dimethylaminomethyl, the dotted line is a single bond and R is cyano or halogen, preferably cyano.

In a further embodiment of the invention the compound of formula (IV) in the method for isolation and purification above, is a compound wherein Y is O, or S, preferably Y is O and the other substituents are as defined above. In a further embodiment of the invention the compound of formula (IV) in the method for isolation and purification above, is a compound, wherein Y is S.

In a further embodiment of the invention the compound of formula (IV) in the method for isolation and purification above, is a compound wherein Y is a bond and the other substituents are as defined above.

In a further embodiment of the invention the compound of formula (IV) in the method for isolation and purification above, is a compound wherein Y is NH and the other substituents are as defined above.

In a preferred embodiment of the invention, the compound of formula (IV) in the method for isolation and purification above, is a compound wherein $R^1$ is $C_{1-6}$-alkyl, $C_{2-6}$-alkenyl or $C_{2-6}$-alkynyl all of which may optionally be substituted one or more times with substituents selected from $C_{1-6}$-alkoxy, $C_{1-6}$-alkylthio, hydroxy, halogen, amino, nitro, cyano, $C_{1-6}$-alkylamino and di-($C_{1-6}$-alkyl)amino, more preferred $R^1$ is $C_{1-4}$-alkyl, $C_{2-4}$-alkenyl or $C_{2-4}$-alkynyl all of which may optionally be substituted one or more times with substituents selected from $C_{1-4}$-alkoxy, $C_{1-4}$-alkylthio, hydroxy, halogen, amino, nitro, cyano, $C_{1-4}$-alkylamino and di-($C_{1-4}$-alkyl)amino, preferably $R^1$ is $C_{1-3}$-alkyl, $C_{2-3}$-alkenyl or $C_{2-3}$-alkynyl all of which may optionally be substituted one or more times with substituents selected from $C_{1-3}$-alkoxy, $C_{1-3}$-alkylthio, hydroxy, halogen, amino, nitro, cyano, $C_{1-3}$-alkylamino and di-($C_{1-3}$-alkylamino and most preferred $R^1$ is $C_{1-3}$-alkyl, in particular unbranched $C_{1-3}$-alkyl.

In another preferred embodiment of the invention, the compound of formula (IV) in the method for isolation and purification above, is a compound wherein $R^1$ is as follows: $C_{1-10}$-alkyl, $C_{2-10}$-alkenyl or $C_{2-10}$-alkynyl all of which may optionally be substituted one or more times with substituents selected from $C_{1-10}$-alkoxy, $C_{1-10}$-alkylthio, hydroxy, halogen, amino, nitro, cyano, $C_{1-6}$-alkylamino and di-($C_{1-10}$-alkyl)amino, more suitable $R^1$ is $C_{2-10}$-alkenyl or $C_{2-10}$-alkynyl all of which may optionally be substituted one or more times with substituents selected from hydroxy, halogen, amino, nitro and cyano, preferably $R^1$ is $C_{1-10}$-alkyl, preferably unbranched $C_{1-10}$-alkyl and more preferred $R^1$ is unbranched $C_{4-10}$-alkyl As an protic organic solvent which may be used in the isolation and purification step, there may be mentioned, for example, alcohols such as methanol, ethanol, 1-propanol, 2-propanol, 1-butanol, 2-butanol and tert-butanol. The above solvents may be used singly or in a combination of two or more species.

As an apolar organic solvent which may be used in the isolation and purification step, there may be mentioned, for example, hydrocarbons such as hexane, heptane, benzene and toluene; ethers such as diethyl ether, tert-butyl methyl ether and dimethoxyethane; halogenated hydrocarbons such as methylene chloride, chloroform and 1,1,1-trichloroethane. Among them, preferred are hydrocarbons such as hexane; heptane, benzene and toluene, and more preferred is heptane. The above solvents may be used singly or in a combination of two or more species.

According to a specific embodiment of the invention, the mixture of the compound of formula (IV) and the diol of formula (II) used in the above method for isolation and purification has been prepared by enzymatic acylation according to the invention and in another embodiment by enzymatic deacylation according to the invention.

The optical purity of the product obtained after separation of the enantiomers of formula (II) and (IV) as above, may have to be improved before further processing. Improvement of the optical purity may be obtained by chromatography as described in WO 03/006449 or by crystallisation of diastereomeric esters or salts with optically active acids as described in U.S. Pat. No. 4,943,590.

The present invention also relates to a process for the preparation of escitalopram having the formula

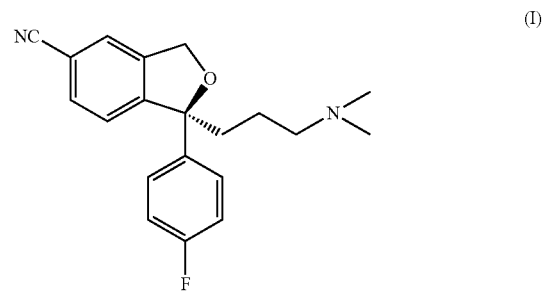

(I)

or a pharmaceutically acceptable salt thereof comprising preparation of the S-enantiomer of a diol having the formula

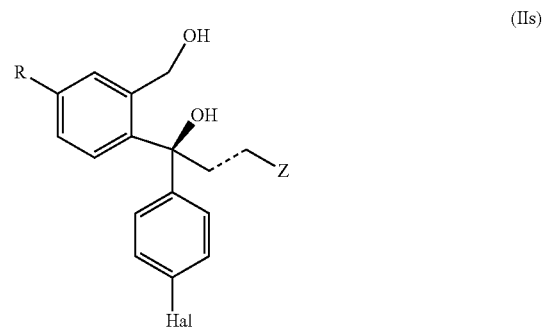

(IIs)

wherein R is cyano or a group which may be converted to a cyano group, the dotted line represents a double or a single bond, Z is a dimethylaminomethyl group or a group which may be converted to a dimethylaminomethyl group and Hal is halogen, or a salt thereof, or the S-enantiomer of an acylated diol having the formula

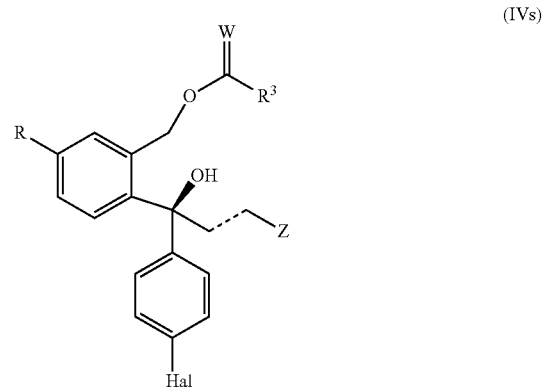

(IVs)

wherein R, Z, the dotted line and Hal are as defined above, W is O or S, and $R^3$ is —Y—$R^1$, wherein $R^1$ is $C_{1-10}$-alkyl, $C_{2-10}$-alkenyl or $C_{2-10}$-alkynyl all of which may optionally be substituted one or more times with substituents selected from $C_{1-10}$-alkoxy, $C_{1-10}$-alkylthio, hydroxy, halogen, amino, nitro, cyano, $C_{1-10}$-alkylamino, di-($C_{1-10}$-alkyl)amino, aryl, aryloxy, arylthio and heteroaryl, or $R^1$ is aryl, wherein any of the aryl and heteroaryl groups may optionally be substituted one or more times with substituents selected from $C_{1-10}$- alkyl, $C_{2\text{-}10}$-alkenyl, $C_{2\text{-}10}$-alkynyl, $C_{1\text{-}10}$-alkoxy, $C_{1\text{-}10}$-alkylthio, hydroxy, halogen, amino, nitro, cyano, $C_{1\text{-}10}$-alkylamino and di-$(C_{1\text{-}10}$-alkyl)amino and Y is a bond, O, S or NH or a salt thereof, in one embodiment by the method for selective enzymatic acylation according to the invention as defined in any of the embodiments above and in another embodiment by the method for selective enzymatic deacylation according to the invention as defined in any of the embodiments above, optionally followed by, in either order, conversion of the group R to a cyano group, reduction of a double bond represented by the dotted line, conversion of the group Z to a dimethylaminomethyl group and/or conversion of the group Hal to a fluoro group and ring closure under basic conditions of the S-enantiomer of formula (IIs) or (IVs) or a labile ester derivative thereof to form a compound of formula

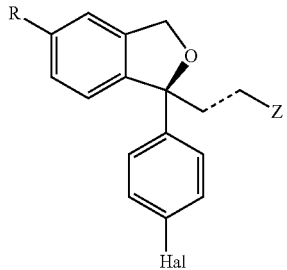

(V)

followed by, in either order; if R is not cyano conversion of the group R to a cyano group, if the dotted line represents a double bond reduction to a single bond, if Z is not dimethylaminomethyl conversion of the group Z to a dimethylaminomethyl group and if Hal is not fluoro, conversion of Hal to a fluoro group, followed by isolation of escitalopram or a pharmaceutically acceptable salt thereof.

According to one embodiment of the invention, the S-enantiomer of formula (IIs) above or the S-enantiomer of formula (IVs) used for the preparation of escitalopram is separated from the R-enantiomer of formula (IV) and (II) respectively, before ringclosure.

According to one embodiment of the above method for the preparation of escitalopram the mixture of the R- or S-enantiomer of a compound of formula (II) and the opposite enantiomer of the compound of formula (IV) obtained by enzymatic acylation has been separated from each other by the isolation and purification process according one of the above novel methods for isolation and purification. According to another embodiment, the mixture has been separated by the other of the above novel methods for isolation and purification.

According to still another embodiment of the above method for the preparation of escitalopram the mixture of the R- or S-enantiomer of a compound of formula (II) and the opposite enantiomer of the compound of formula (IV) obtained by enzymatic deacylation has been separated from each other by the isolation and purification process according one of the above novel methods for isolation and purification. According to another embodiment, the mixture has been separated by the other of the above novel methods for isolation and purification.

According to another embodiment of the invention, the S-enantiomer of formula (IIs) above or the S-enantiomer of formula (IVs) used for the preparation of escitalopram is not separated from the R-enantiomer of formula (IV) and (II) respectively, before ringclosure.

As mentioned above, the group R means cyano or any other group which may be converted to a cyano group.

Groups which may be converted to a cyano group include halogen such as chloro, bromo, iodo or fluoro, preferably chloro or bromo.

Other groups which may be converted to cyano include $CF_3$—$(CF_2)_n$—$SO_2$—O—, wherein n is 0-8, —OH, —CHO, —$CH_2OH$, —$CH_2NH_2$, —$CH_2NO_2$, —$CH_2Cl$, —$CH_2Br$, —$CH_3$, —$NHR^5$, —CHNOH, —$COOR^6$, —$CONR^6R^7$ wherein $R^5$ is hydrogen or $C_{1\text{-}6}$ alkylcarbonyl, and $R^6$ and $R^7$ are selected from hydrogen, optionally substituted $C_{1\text{-}6}$ alkyl, aryl-$C_{1\text{-}6}$ alkyl or aryl and, a group of formula

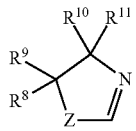

(VII)

wherein Z is O or S; $R^8$-$R^9$ are each independently selected from hydrogen and $C_{1\text{-}6}$ alkyl or $R^8$ and $R^9$ together form a $C_{2\text{-}5}$ alkylene chain thereby forming a spiro ring; $R^{10}$ is selected from hydrogen and $C_{1\text{-}6}$ alkyl, $R^{11}$ is selected from hydrogen, $C_{1\text{-}6}$ alkyl, a carboxy group or a precursor group therefore, or $R^{10}$ and $R^{11}$ together form a $C_{2\text{-}5}$ alkylene chain thereby forming a spiro ring.

When R is halogen, in particular bromo or chloro, conversion to a cyano may be carried out as described in U.S. Pat. No. 4,136,193, WO 00/13648, WO 00/11926 and WO 01/02383.

According to U.S. Pat. No. 4,136,193 conversion of a bromo group to a cyano group, is carried out by reaction with CuCN.

WO 00/13648 and WO 00/11926 describe the conversion of a halogen or a triflate group to a cyano group by cyanation with a cyanide source in presence of a Pd or Ni catalyst.

Other processes for the conversion of a bromo compound to the corresponding cyano derivative involve reaction of the bromo compound with magnesium to form a Grignard reagent, followed by reaction with a formamide to form an aldehyde. The aldehyde is converted to an oxime or a hydrazone which is converted to a cyano group by dehydration and oxidation, respectively.

Alternatively, the bromo compound is reacted with magnesium to form a Grignard reagent, followed by reaction with a compound containing a CN group bound to a leaving group.

A detailed description of the above two procedures may be found in WO 01/02383.

Compounds wherein the group R is —CHO, may be converted to the corresponding compounds wherein R is cyano by methods analogous to those described in WO 99/00210.

Compounds wherein the group R is $NHR^{12}$, wherein $R^{12}$ is hydrogen or alkylcarbonyl, may be converted to the corresponding compounds wherein the group R is cyano by methods analogous to those described in WO 98/19512.

Compounds wherein R is a —$COOR^6$ group, may be converted to the corresponding compound wherein R is cyano by conversion to the amide via the corresponding acid chloride or an ester thereof followed by dehydration of the amide. WO 01/68632.

Alternatively, a compound where R is —COOH may be reacted with chlorosulfonyl isocyanate in order to form the nitrile, or treated with a dehydrating agent and a sulfonamide as described in WO 00/44738.

Compounds wherein the group R is —CONR$^{13}$R$^{14}$, wherein R$^{13}$ and R$^{14}$ are selected from hydrogen optionally substituted alkyl, aralkyl or aryl may be converted to the corresponding cyano compound by methods analogous to those described in WO 98/00081 and WO 98/19511.

Compounds wherein the group R is a group of formula (VII) may be converted to the corresponding cyano compound by methods analogous to those described in WO 00/23431.

Compounds wherein R is OH, —CH$_2$OH, —CH$_2$NH$_2$, —CH$_2$NO$_2$, —CH$_2$Cl, —CH$_2$Br, —CH$_3$ or any of the groups above, may be converted to the corresponding cyano compounds by methods analogous to those described in WO 01/68632.

Racemic compounds of formula (II) may be prepared by the methods described in the above mentioned patents or by the alkylation method described in U.S. Pat. No. 4,136,193 or the double grignard reaction described in EP 171 943 or by analogous methods. Racemic compounds of formula (IV) may be prepared from racemic compounds of formula (II) by non-selective acylation using anhydrides, esters, carbonates, isocyanates or isothiocyanates as defined by formulas (IIIa), (IIIb), (IIIc), R$^1$—N=C=O and R$^1$—N=C=S above.

In some cases the racemic compound of formula (II) may be available in the form of an acid addition salt, such as the sulphate salt, and in this case a free base of the compound of formula (II) may be obtained by treating the salt with a base in a mixture or water and an organic solvent, to transfer the compound of formula (II) into the organic phase.

Preferably, R is cyano in the compounds of formula (II), (IIs), (IIr), (IV) (IVs) (IVr) and (V). If R is not cyano, conversion of the group R to a cyano group is suitably carried out after ringclosure to form a compound of formula (V).

Preferably, Hal is fluoro in the compounds of formula (II), (IIs), (IIr), (IV) (IVs) (IVr) and (V). If Hal is not fluoro, conversion of the group Hal to a fluoro is suitably carried out after ringclosure to form a compound of formula (V). A procedure for carrying out this conversion is described in Speciality Chemicals Magazine, April 2003, page 36-38.

Z groups which may be converted to dimethylaminomethyl are groups such as —CH$_2$-L, —CH$_2$—NO$_2$, —MgHal, cyano, aldehyde, —CH$_2$—O-Pg, —CH$_2$—NPg$_1$Pg$_2$, —CH$_2$—NMePg$_1$, —CH$_2$—NHCH$_3$, —CH$_2$—NH$_2$, —CO—N(CH$_3$)$_2$, —CH(A$^1$R$^{12}$)(A$^1$R$^{13}$), -(A$^1$R$^{14}$)(A$^2$R$^{15}$) (A$^3$R$^{16}$), —COOR$^{17}$, —CH$_2$—CO—NH$_2$, —CH=CH—R$^{18}$ or —CONHR$^{19}$, wherein Pg is a protection group for an alcohol group, Pg$_1$ and Pg$_2$ are protection groups for an amino group, R$^{12}$ and R$^{13}$ are independently selected from C$_{1-6}$ alkyl, C$_{2-6}$ alkenyl, C$_{2-6}$ alkynyl and optionally alkyl substituted aryl or aralkyl groups or R$^{12}$ and R$^{13}$ together form a chain of 2 to 4 carbon atoms, each of R$^{14}$-R$^{18}$ are independently selected from C$_{1-6}$ alkyl, C$_{2-6}$ alkenyl, 2$_{1-6}$ alkynyl and optionally C$_{1-6}$ alkyl substituted aryl or aryl-C$_{1-6}$ alkyl, R$^{19}$ is hydrogen or methyl and A$^1$, A$^2$ and A$^3$ are selected form O and S; L is a leaving group, such as halogen or —O—SO$_2$-A wherein A is C$_{1-6}$ alkyl, C$_{2-6}$ alkenyl, C$_{2-6}$ alkynyl or optionally C$_{1-6}$ alkyl substituted aryl or aryl-C$_{1-6}$ alkyl.

In one embodiment of the invention Z is dimethylaminomethyl, —CH$_2$-L, —CH$_2$—NPg$_1$Pg$_2$, —CH$_2$—NMePg$_1$, —CH$_2$—NHCH$_3$, —CH$_2$—NH$_2$, —CO—N(CH$_3$)$_2$, aldehyde or —COOR$^{17}$ in the compounds of formula (II), (IIs), (IIr), (IV) (IVs) (IVr) and (V).

Compounds wherein Z is —CH$_2$—O-Pg may be converted to the corresponding compounds wherein Z is dimethylaminomethyl by removal of the protection group to form the corresponding alcohol and thereafter conversion of the alcohol group to a feasible leaving group and reaction of the resulting compound with a) dimethylamine or a salt thereof, b) methylamine followed by methylation or reductive amination, or c) with an azide followed by reduction to form the corresponding amine and thereafter methylation or reductive amination, as described in WO 01/43525, WO 01/51478 or WO 01/68631 or by analogous methods.

Compounds wherein Z is —CH$_2$-L, wherein L is a leaving group, may be converted to a dimethylaminomethyl group in the same manner.

Compounds wherein Z is —CO—N(CH$_3$)$_2$ and —CO—NHR$^{19}$, wherein R$^{19}$ is hydrogen or methyl, may be converted to the corresponding compounds wherein Z is dimethylaminomethyl by reduction of the amide and if a primary or secondary amine is formed, followed by methylation or reductive amination to form a dimethylaminomethyl group as described in WO 01/43525 or WO 01/68631 or by analogous methods.

Compounds wherein Z is —CH$_2$—NMe(Pg$_1$) or —CH$_2$—N(Pg1)(Pg2) may be converted to the corresponding compound wherein Z is dimethylaminomethyl by removal of the protection groups, i.e. to obtain compounds wherein Z is —CH$_2$—NH$_2$ or —CH$_2$—NMe and thereafter methylation of the amino group or reductive amination to form a dimethyaminomethyl group as described in WO 01/43525 or WO 01/68631 or by analogous methods.

Compounds wherein Z is —CH(A$^1$R$^{12}$)(A$^2$R$^{13}$) may be converted to the corresponding compounds wherein Z is dimethylaminomethyl by deprotection to form an aldehyde (compounds where Z is —CH$_2$—CA$^1$H) followed reductive amination with dimethylamine to form a dimethylaminomethyl group as described in WO 01/43525 or WO 01/68631 or by analogous methods.

Compounds wherein Z is —C(A$^1$R$^{14}$)(A$^2$R$^{15}$)(A$^3$R$^{16}$) may be converted to the corresponding compounds wherein Z is dimethylaminomethyl i) by hydrolysis to form a carboxylic acid or an ester thereof and thereafter reduction to form an alcohol and thereafter conversion of the alcohol group to a feasible leaving group, followed by replacement of the leaving group with a dimethylamino group as described above, or ii) conversion of the carboxylic acid or an ester thereof to an amide by reaction with an amine of NH(Me)$_2$, NH$_2$Me, NH$_3$ or a salt thereof followed by, in either order, reduction of the amide and if necessary methylation or reductive amination to form a dimethylamino group as described in WO 01/68631 or by analogous methods.

Compounds wherein Z is —COOR$^{17}$ may be converted to the corresponding compounds wherein Z is dimethylaminomethyl as described above, starting with the carboxylic acid ester.

Compounds wherein Z is —CH$_2$—CONH$_2$ may be converted to the corresponding compound wherein Z is dimethylaminomethyl by treatment with hypohalide to form a primary amine followed by methylation of the free amino group or reductive amination to form a dimethylaminomethyl group as described in WO 01/43525 or WO 01/68631 or by analogous methods.

Compounds wherein Z is —CH=CHR$^{18}$ may be converted to the corresponding compound wherein Z is dimethylaminomethyl by oxidation to form an aldehyde which may be converted to dimethylaminomethyl by reductive amination as described in WO 01/43525 or WO 01/68631 or by analogous methods.

Compounds wherein Z is cyano or —CH$_2$—NO$_2$ may be converted to the corresponding compound wherein Z is dimethylaminomethyl by reduction followed by methylation or reductive amination of the free of the amino group formed to form dimethylaminomethyl as described in WO 01/68629 or by analogous methods.

Compounds wherein Z is —MgHal may be converted to the corresponding compound wherein Z is dimethylaminomethyl by reaction with dimethylaminomethyl alkyl ether of formula (CH$_3$)$_2$NCH$_2$O-alkyl as described in WO 01/68629 or by analogous methods.

Preferably, Z is dimethylaminomethyl. If Z is not dimethylaminomethyl, conversion of Z to a dimethylaminomethyl group is suitably carried out after ringclosure.

Suitably, Z is dimethylaminomethyl, —CH$_2$-L, —CH$_2$—NPg$_1$Pg$_2$, —CH$_2$—NMePg$_1$, —CH$_2$—NHCH$_3$, —CH$_2$—NH$_2$, aldehyde, —CO—N(CH$_3$)$_2$, —COOR$^{17}$ when the dotted line represents a bond.

Compounds of formula (II) or (IV) wherein Z is dimethylaminomethyl, CH$_2$—NPg$_1$Pg$_2$, —CH$_2$—NMePg$_1$, —CH$_2$—NHCH$_3$, or —CH$_2$—NH$_2$, in particular compounds wherein Z is dimethylaminomethyl, —CH$_2$—NHCH$_3$, or —CH$_2$—NH$_2$, are particularly well suited for the method of purification isolation according to the invention, wherein the compounds of formula (II) and (IV) are separated.

In the compounds of formula (II), (IIs), (IIr), (IV) (IVs) (IVr) and (V), the dotted line is preferably a single bond. Compounds wherein the dotted line represents a double bond may be converted to the corresponding compound wherein the dotted line is a single bond by the methods described in WO 01/68630. Preferably the reduction is carried out after ringclosure.

Enantioselective ring-closure of the compounds of formula (IVs) or (IIs) to form the compounds of formula (V) may suitably be carried out by treatment of a labile ester derivative of the compound with a base such as KOC(CH$_3$)$_3$ and other alkoxides, NaH and other hydrides, triethylamine, ethyldiisopropylamine or pyridine, at low temperatures in an inert organic solvent, such as tetrahydrofuran, toluene, DMSO, DMF, t-butyl methyl ether, dimethoxyethane, dimethoxymethane, dioxane, acetonitrile or dichloromethane. This process is described in U.S. Pat. No. 4,943,590.

Ringclosure of the compound of formula (IIs), is suitably carried out by treatment with a base as described above in presence of an agent capable of forming a labile group with the primary alcohol of the diol, such as methanesulfonyloxy, p-toluenesulfonyloxy, 10-camphorsulfonyloxy, trifluoroacetyloxy and trifluoromethanesulfonyloxy and halogen.

In some cases, it may be advantageous to exchange the —W—R$^3$ group in the compound of formula (IVs), for a more labile group before ringclosure is carried out. Such labile groups (leaving groups) could typically be a group selected from methanesulfonyloxy, p-toluenesulfonyloxy, 10-camphorsulfonyloxy, trifluoroacetyloxy and trifluoromethanesulfonyloxy or halogen.

Typically, the compound of formula (IVs) is subjected to hydrolysis to form the compound of formula (IIs) with aqueous base, such as NaOH, KOH or LiOH in water or alcohol or a mixture thereof and then reacted with an activated leaving group, such as for example mesylchloride or tosylchloride in an organic solvent in the presence of an organic base.

The optical purity of the escitalopram product may have to be improved after ringclosure. Improvement of the optical purity may be obtained by chromatography on a chiral stationary phase or by crystallisation of racemic citalopram base or a salt thereof according to the methods described in WO 03/000672.

The R-enantiomer of the compounds of formula (II) and (IV) obtained according to the invention may be used to prepare racemic citalopram and escitalopram by ring closure in acidic environment according to the method described in WO 03/000672. Suitable acids for carrying out acidic ring closure are mineral acid, a carboxylic acid, a sulfonic acid or sulfonic acid derivative, more suitable H$_2$SO$_4$ or H$_3$PO$_4$.

Thus in another embodiment, the invention relates to a process for the preparation of racemic citalopram and/or escitalopram or a pharmaceutically acceptable salt thereof comprising preparation of the R-enantiomer of a diol having the formula

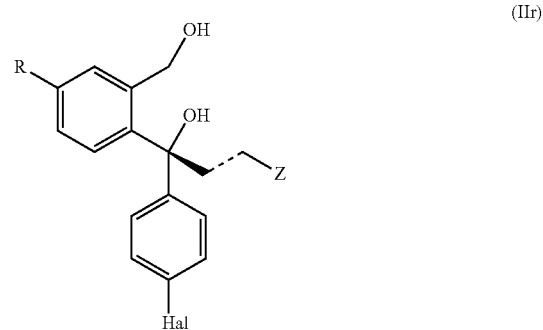

(IIr)

wherein R is cyano or a group which may be converted to a cyano group, the dotted line represents an optinal bond and Z is a dimethylaminomethyl group or a group which may be converted to a dimethylaminomethyl group and Hal is halogen, or a salt thereof, or the R-enantiomer of an acylated diol having the formula

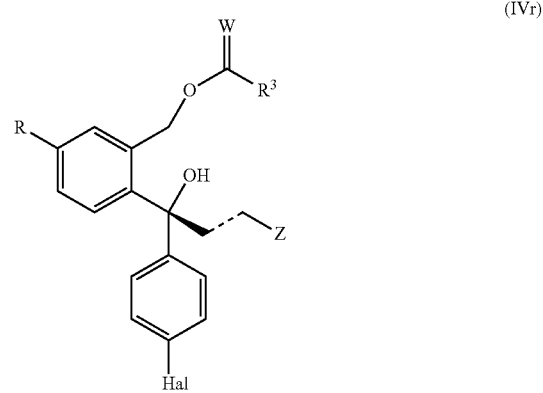

(IVr)

wherein R, Z, the dotted line and Hal is as defined above, W is O or S, and R$^3$ is —Y—R$^1$, wherein R$^1$ is C$_{1-10}$-alkyl, C$_{2-10}$-alkenyl or C$_{2-10}$-alkynyl all of which may optionally be substituted one or more times with substituents selected from C$_{1-10}$-alkoxy, C$_{1-10}$-alkylthio, hydroxy, halogen, amino, nitro, cyano, C$_{1-10}$-alkylamino, di-(C$_{1-10}$-alkyl)amino, aryl, aryloxy, arylthio and heteroaryl, or R$^1$ is aryl, wherein any of the aryl and heteroaryl groups may optionally be substituted one or more times with substituents selected from C$_{1-10}$-alkyl, C$_{2-10}$-alkenyl, C$_{2-10}$-alkynyl, C$_{1-10}$-alkoxy, C$_{1-10}$-alkylthio, hydroxy, halogen, amino, nitro, cyano, C$_{1-10}$-alkylamino and di-($C_{1-10}$-alkyl)amino and Y is a bond, O, S or NH, or a salt thereof, in one embodiment by the method for selective enzymatic acylation according to the invention as defined in any of the embodiments above and in another embodiment by the method for selective enzymatic deacylation according to the invention as defined in any of the embodiments above, optionally followed by, in either order, conversion of the group R to a cyano group, reduction of a double bond represented by the dotted line to a single bond, conversion of the group Z to a dimethylaminomethyl group and/or conversion of the group Hal to a fluoro group and ringclosure under acidic conditions of the R-enantiomer of formula (IIr) or (IVs) to form a mixture of the compound of formula

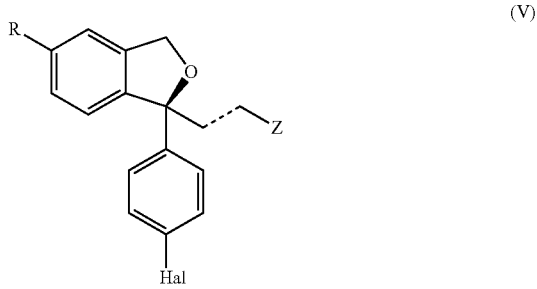

(V)

wherein Hal, Z, R and the dotted line are as defined above, and a minor amount of the corresponding R-enantiomer, followed by, in either order; if R is not cyano conversion of the group R to a cyano group, if the dotted line represents a double bond reduction to a single bond, if Z is not dimethylaminomethyl conversion of the group Z to a dimethylaminomethyl group and if Hal is not fluoro, conversion of Hal to a fluoro group, followed by isolation of escitalopram and/or racemic citalopram or a pharmaceutically acceptable salt thereof, by precipitation of racemic citalopram free base or a salt thereof and recovery of escitalopram form the mother liquor of the precipitation.

Suitably, the above method for conversion of R-diol to escitalopram, is used for the preparation of escitalopram.

The conversion of of the group R to a cyano group, reduction of a double bond represented by the dotted line to a single bond, conversion of the group Z to a dimethylaminomethyl group and conversion of Hal to a fluoro group may be carried out as described above.

According to one embodiment of the above method for the preparation of escitalopram the mixture of the R- or S-enantiomer of a compound of formula (II) and the opposite enantiomer of the compound of formula (IV) obtained by enzymatic acylation has been separated from each other by the isolation and purification process according one of the above methods for isolation and purification. According to another embodiment, the mixture has been separated by the other of the above methods for isolation and purification.

According to still another embodiment of the above method for the preparation of escitalopram the mixture of the R- or S-enantiomer of a compound of formula (II) and the opposite enantiomer of the compound of formula (IV) obtained by enzymatic deacylation has been separated from each other by the isolation and purification process according one of the above methods for isolation and purification. According to another embodiment, the mixture has been separated by the other of the above methods for isolation and purification.

According to another embodiment of the invention, the S-enantiomer of formula (IIr) above or the S-enantiomer of formula (IVr) used for the preparation of escitalopram is not separated form the R-enantiomer of formula (IV) and (II) respectively, before ringclosure.

The optical purity of the escitalopram product may have to be improved after ringclosure. Improvement of the optical purity may be obtained by chromatography on a chiral stationary phase or by crystallisation of racemic citalopram base or a salt thereof according to the methods described in WO 03/000672.

As used herein, the term $C_{1-10}$-alkyl refers to a branched or unbranched alkyl group having from one to ten carbon atoms inclusive, such as methyl, ethyl, 1-propyl, 2-propyl, 1-butyl, 2-butyl, 2-methyl-2-propyl, 2-methyl-1-propyl, pentyl, hexyl and heptyl. $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2-methyl-1-propyl, pentyl and hexyl. $C_{1-4}$-alkyl refers to a branched or unbranched alkyl group having from one to four carbon atoms inclusive, such as methyl, ethyl, 1-propyl, 2-propyl, 1-butyl, 2-butyl, 2-methyl-2-propyl and 2-methyl-1-propyl. $C_{1-3}$-alkyl refers to a branched or unbranched alkyl group having from one to three carbon atoms inclusive, such as methyl, ethyl, 1-propyl, 2-propyl.

Similarly, $C_{2-10}$-alkenyl and $C_{2-10}$-alkynyl designate branched or unbranched alkenyl and alkynyl groups, respectively, having from two to ten carbon atoms, including one double bond and one triple bond respectively, such as ethenyl, propenyl, butenyl, ethynyl, propynyl and butynyl. $C_{2-6}$-alkenyl and $C_{2-6}$-alkynyl designate branched or unbranched alkenyl and alkynyl groups, respectively, having from two to six carbon atoms, including one double bond and one triple bond respectively, such as ethenyl, propenyl, butenyl, ethynyl, propynyl and butynyl. $C_{2-4}$-alkenyl and $C_{2-4}$-alkynyl designate branched or unbranched alkenyl and alkynyl groups, respectively, having from two to four carbon atoms, including one double bond and one triple bond respectively, such as ethenyl, propenyl, butenyl, ethynyl, propynyl and butynyl. $C_{2-3}$-alkenyl and $C_{2-3}$-alkynyl designate branched or unbranched alkenyl and alkynyl groups, respectively, having from two to three carbon atoms, including one double bond and one triple bond respectively, such as ethenyl, propenyl, ethynyl and propynyl.

The terms $C_{1-10}$ alkoxy, $C_{1-10}$ alkylthio, $C_{1-10}$ alkylamino and di-($C_{1-10}$-alkylamino etc. designate such groups in which the alkyl group is $C_{1-10}$ alkyl as defined above. The terms $C_{1-6}$ alkoxy, $C_{1-6}$ alkylthio, $C_{1-6}$ alkylamino and di-($C_{1-6}$-alkyl) amino etc. designate such groups in which the alkyl group is $C_{1-6}$ alkyl as defined above. The terms $C_{1-4}$ alkoxy, $C_{1-4}$ alkylthio, $C_{1-4}$ alkylamino and di-($C_{1-4}$-alkyl)amino etc. designate such groups in which the alkyl group is $C_{1-4}$ alkyl as defined above. The terms $C_{1-3}$ alkoxy, $C_{1-3}$ alkylthio, $C_{1-3}$ alkylamino and di-($C_{1-3}$-alkylamino etc. designate such groups in which the alkyl group is $C_{1-3}$ alkyl as defined above.

Halogen means fluoro, chloro, bromo or iodo.

The term aryl refers to a mono or bicyclic carbocyclic aromatic group, such as phenyl, or naphthyl, in particular phenyl.

Aryloxy, arylthio refers to such a group wherein aryl is as defined above.

The term heteroaryl refers to a 5 or 6 membered monocyclic heteroaromatic group or a bicyclic heteroaromatic group. Suitable the heteroaryl group contains 1-3 heteroatoms selected from O, S and N.

$R^0$ and $R^1$ may together form a chain of 3 to 5 carbon atoms, thus forming an anhydride.

When Z is —CH$_2$—N(R'R") wherein R' and R" connected to each other to form a cyclic structure including the N-atom to which they are attached, the cyclic structure form groups, such as groups include piperidin, pyrrolidin, morpholinyl and piperazinyl.

HOBt means hydroxybenzotriazol and pfp means pentafluorophenol.

Experimentals

In the following examples % conversion and optical purity were measured and calculated as described below:

HPLC analysis condition (for conversion rate) used for examples 1-28:
Column: YMC-Pack ODS-A 0.46 cm I.D.×25 cm (made by YMC Co., LTD.)
Eluent: 25 mM Phosphate buffer/Acetonitrile=60/40
Flow rate: 1.0 ml/min
Temperature: 40° C.
Detector wavelength: 237 nm HPLC analysis condition (for conversion rate) used for examples 29-42:
Column: A Lichrospher RP-8 column, 250×4 mm (5 μm particle size)
Eluent: Buffered MeOH/water prepared as follows: 1.1 ml Et$_3$N added to 150 ml water, 10% H$_3$PO$_4$(aq) is added to pH=7 and water is added to a total of 200 ml. The mixture is added to 1.8 L MeOH.
Temperature: 35° C.
Flow rate: 1 mL/min
Pressure: 16.0 MPa
Detection: UV 254 nm
Injection volume: 10 microL
Conversion rate (%)=P/(S+P)×100, (P: amount of product, S: amount of residual substrate).

HPLC analysis condition (for optical purity) used for examples 1-28:
Column: Chiralpak AD 0.46 cm I.D.×25 cm (made by DAICEL CHEMICAL INDUSTRIES, LTD.)
Eluent: Heptane/methanol/ethanol/diethylamine=85/7.5/7.5/0.1
Flow rate: 1.0 ml/min
Temperature: 30° C.
Detector wavelength: 240 nm
Conversion rate (%)=P/(S+P)×100, (P: amount of product, S: amount of residual substrate)

Super critical fluid chromatography. Analysis condition (for optical purity) used for examples 29-42:
Column: Daicel AD column with the dimensions 250×4.6 mm (5 μm particle size)
Mobile phase: Carbon dioxide
Modifier: Methanol with diethylamine (0.5%) and trifluoroacetic acid (0.5%).
Modifier gradient: 1-2% in 4 minutes
2-4% in 4 minutes
4-8% in 4 minutes
8-16% in 4 minutes
16-32% in 4 minutes
32-45% in 1.62 minutes
Temperature: Ambient temperature
Flow rate: 2 mL/min
Pressure: 20 mPa
Detection: UV 230 nm and 254 nm
Injection volume: 10 microL Optical purity (% ee)=(A−B)/(A+B)×100, (A and B represent corresponding stereo isomer, A>B)

$$E\text{-value}=\ln((1-c/100)\times(1-Es/100))/\ln((1-c/100)\times(1+Es/100))$$

(c: conversion ratio, Es: optical purity of residual substrate)

Example 1

(S)-4-[4-Dimethylamino-1-(4'-fluorophenyl)-1-hydroxybutyl]-3-hydroxymethyl-benzonitrile Water (200.7 g) and toluene (440.8 g) was added to (±)-4-[4-dimethylamino-1-(4'-fluorophenyl)-1-hydroxybutyl]-3-hydroxymethylbenzonitrile, ½ sulfuric acid salt (100.4 g, 0.257 mol), then stirred for 15 minutes and the temperature thereof was raised up to 60° C. Subsequently, 30% NaOH (34.5 g, 0.259 mol) was added dropwise over 5 minutes until pH of aqueous layer reached 11.4, and stirred for 30 minutes. After stirring, the mixture was allowed to stand for 5 minutes, and separated. The aqueous layer was discarded, and thus-obtained organic layer was washed with 220.0 g of water, and further, concentrated under reduced pressure at 60° C. to remove away the remaining moisture. The concentration was adjusted by addition of toluene, to thereby obtain 583.1 g of a solution of 4-[4-dimethylamino-1-(4'-fluorophenyl)-1-hydroxybutyl]-3-hydroxymethylbenzonitrile in toluene (content of pure 4-[4-dimethylamino-1-(4'-fluorophenyl)-1-hydroxybutyl]-3-hydroxymethylbenzonitrile: 87.6 g, yield: 99.7%, 0.256 mol). Then, 52.5 g of toluene was poured onto 17.5 g of an immobilized enzyme (Novozym 435), then 583.1 g of the solution of 4-[4-dimethylamino-1-(4'-fluorophenyl)-1-hydroxybutyl]-3-hydroxymethylbenzonitrile in toluene was added, and the temperature of the mixture was controlled to 40° C. Subsequently, a mixed solution containing pivalic acid (28.7 g, 0.281 mol), vinyl butyrate (29.2 gm 0.256 mol) and toluene (28.8 g) was added into the above mixture over 20 minutes, and the mixture was stirred at 40° C. for 12 hours under a slight flow of nitrogen. After cooling the mixture over 2 hours so as to be 20° C., the mixture was stirred for 1 hour at the same temperature, and stirring was stopped. The enzyme was filtrated, and then the enzyme was washed twice with 105 g of toluene, and these toluene layers were combined. The toluene layer contained 583.1 g of a solution of 4-[4-dimethylamino-1-(4'-fluorophenyl)-1-hydroxybutyl]-3-hydroxymethylbenzonitrile in toluene (content of pure (S)-4-[4-dimethylamino-1-(4'-fluorophenyl)-1-hydroxybutyl]-3-hydroxymethylbenzonitrile: 36.0 g, yield through the enzymatic resolution process: 41.1%, 0.105 mol).

A mixed solution containing the supernatant and washing fluid was extracted three times with water (438 g, 263 g×2), and 1005.4 g of the obtained aqueous layer was washed with 79 g of toluene for five times. As a result, it was obtained 985.2 g of an aqueous solution of (S)-4-[4-dimethylamino-1-(4'-fluorophenyl)-1-hydroxybutyl]-3-hydroxymethylbenzonitrile, pivalic acid salt {content of pure (S)-4-[4-dimethylamino-1-(4'-fluorophenyl)-1-hydroxybutyl]-3-hydroxymethylbenzonitrile: 32.6 g, yield (through the process from the extraction with water to washing with toluene): 90.6%, 0.0952 mol}. To thus-obtained 985.2 g of an aqueous solution of (S)-4-[4-dimethylamino-1-(4'-fluorophenyl)-1-hydroxybutyl]-3-hydroxymethylbenzonitrile, pivalic acid salt was added 218.2 g of toluene. Subsequently, 30% NaOH (13.3 g, 0.0998 mol) was slowly added to the mixture with stirring, until pH of aqueous layer reached 11.9, and the mixture was kept stirred for 30 minutes. After stirring, the mixture was allowed to stand 30 minutes and the toluene layer was separated, and the remaining aqueous layer was re-extracted with 142.5 g of toluene. The combined toluene layer was washed twice with 169.0 g of water, concentrated at 60° C. under reduced pressure, to thereby obtain 64.0 g of a solution of (S)-4-[4-dimethylamino-1-(4'-fluorophenyl)-1-hydroxybutyl]-3-hydroxymethylbenzonitrile in toluene. Said toluene solution contained 32.0 g (0.0935 mol) of (S)-4-[4-dimethylamino-1-(4'-fluorophenyl)-1-hydroxybutyl]-3-hydroxymethylbenzonitrile. Overall yield was 36.4%. The optical purity determined by HPLC was 98.7% ee, and chemical purity was 99.9 area %, {(R)-5-cyano-2-[dimethylamino-(4'-fluorophenyl)-hydroxybutyl]benzyl butyrate: 0.04 area %.

In the above system, the above "chemical purity" is represented by the following equation.

(Chemical purity)=[Area value of 4-[4-dimethylamino-1-(4'-fluorophenyl)-1-hydroxybutyl]-3-hydroxymethylbenzonitrile]/[(Area value of all detected compounds)−(Area value of toluene)−(Area value derived from the system)]×100 (area %)

Example 2

A test tube equipped with a stopper was charged with 50 mg (0.146 m mol) of (±)-4-[4-dimethylamino-1-(4'-fluorophenyl)-1-hydroxybutyl]-3-hydroxymethylbenzonitrile, 25 mg of various kinds of lipases, 33 mg (0.29 m mol) of vinyl butyrate and 1 ml of toluene, and stirred at 40° C. for 16 hours. For the substrate with the optical purity of at least 50% ee, E-values were calculated. The results are shown in Table 1.

TABLE 1

| Enzyme | Origin | Conversion (%) | Optical purity (% e.e.) | Configuration | E-value |
|---|---|---|---|---|---|
| Lipozyme TL IM (made by Novozymes A/S j | Thermomyces lanuginosus | 97.8 | 62.7 | (R) | 1 |
| Novozym 435 (made by Novozymes A/S j | Candida antarctica | 59.7 | 96.4 | (S) | 18 |
| None | | 1.16 | | | |

Example 3

A test tube equipped with a stopper was charged with 10 to 100 mg (0.029 to 0.29 m mol) of (±)-4-[4-dimethylamino-1-(4'-fluorophenyl)-1-hydroxybutyl]-3-hydroxymethylbenzonitrile, 10 to 100 mg of Novozym 435 (product of Novozymes, E/S ratio=1.0), 33 to 333 mg (10 eq.) of vinyl butyrate and 1 ml of toluene, and stirred at 30° C. for 16 hours. The results are shown in Table 2.

TABLE 2

| Concentration (%) | Conversion (%) | Optical purity (% e.e.) | Configuration | E-value |
|---|---|---|---|---|
| 1 | 52.9 | 93.7 | (S) | 38 |
| 2 | 54.2 | 88.6 | (S) | 20 |
| 5 | 63.1 | 87.9 | (S) | 9 |
| 10 | 65.0 | 92.6 | (S) | 9 |

Example 4

A test tube equipped with a stopper was charged with 100 mg (0.292 m mol) of (±)-4-[4-dimethylamino-1-(4'-fluorophenyl)-1-hydroxybutyl]-3-hydroxymethyl-benzonitrile, 50 mg of Novozym 435 (product of Novozymes), 333 mg (2.92 m mol) of vinyl butyrate, 0.292 m mol of various kinds of additives and 1 ml of toluene, and stirred at the temperature of 40° C. for 16 hours. The results are shown in Table 3.

TABLE 3

| Additive | Conversion (%) | Optical purity (% e.e.) | Configuration | E-value |
|---|---|---|---|---|
| Sulfric acid | 39.8 | 14.7 | (S) | 2 |
| Acetic acid | 34.4 | 46.0 | (S) | 24 |
| Hydrochloric acid | 27.1 | 16.2 | (S) | 3 |
| Benzoic acid | 62.9 | 98.2 | (S) | 16 |
| Triethylamine | 74.8 | 99.7 | (S) | 11 |
| Pyridine | 65.4 | 96.5 | (S) | 11 |
| Benzoic acid ATriethylamine | 66.0 | 92.0 | (S) | 8 |
| Benzoic acid APyridine | 58.1 | 97.3 | (S) | 23 |
| None | 73.5 | 97.4 | (S) | 8 |

Example 5

In a 200-ml four-necked flask equipped with a stirrer and a thermometer, 1.5 g (4.38 in mol) of (±)-4-[4-dimethylamino-1-(4'-fluorophenyl)-1-hydroxybutyl]-3-hydroxymethylbenzonitrile was dissolved in 30 ml of toluene, then 0.45 g of Novozym 435 (product of Novozymes), 0.347 g (4.38 m mol) of pyridine, 4.38 m mol of various kinds of acids and 1.00 g (8.76 m mol) of vinyl butyrate were added, and stirred at 40° C. for between 16 and 21.5 hours. The result is shown in Table 4.

TABLE 4

| Acid | Conversion (%) | Optical purity (% e.e.) | Configuration | E-value |
|---|---|---|---|---|
| Salicylic acid | 54.7 | 95.9 | (S) | 33 |
| p-Ethylbenzoic acid | 64.9 | 97.5 | (S) | 13 |
| o-Toluic acid | 64.5 | 97.3 | (S) | 13 |
| m-Toluic acid | 66.3 | 96.6 | (S) | 11 |
| p-Toluic acid | 55.4 | 98.9 | (S) | 44 |
| o-Anisic acid | 59.3 | 94.9 | (S) | 17 |
| 4-Chlorophenylacetic acid | 59.5 | 96.3 | (S) | 18 |
| 3-Phenylpropionic acid | 46.2 | 74.4 | (S) | 31 |
| 1-Naphthoic acid | 67.8 | 83.3 | (S) | 6 |
| Benzoic acid | 59.7 | 99.9 | (S) | 37 |
| Butyric acid | 53.7 | 89.6 | (S) | 24 |
| Isobutyric acid | 61.8 | 97.1 | (S) | 16 |
| Isovaleric acid | 55.3 | 94.8 | (S) | 27 |
| Pivalic acid | 58.2 | 97.8 | (S) | 25 |
| Caproic acid | 60.3 | 96.1 | (S) | 17 |
| Cyclohexanecarboxylic acid | 55.2 | 95.4 | (S) | 30 |
| None | 59.1 | 95.5 | (S) | 18 |

Example 6

In a 200-ml four-necked flask equipped with a stirrer and a thermometer, 3.0 g (8.76 in mol) of (±)-4-[4-dimethylamino-1-(4'-fluorophenyl)-1-hydroxybutyl]-3-hydroxymethylbenzonitrile was dissolved in 30 ml of toluene, then 0.9 g of Novozym 435 (product of Novozymes), 0.693 g (8.76 m mol) of pyridine, 8.76 m mol of various kinds of acids and 2.00 g (17.52 m mol) of vinyl butyrate were added, and stirred at 40° C. for between 15.5 and 16.5 hours. The results are shown in Table 5.

TABLE 5

| Acid | Reaction time (hrs) | Conversion (%) | Optical purity (% e.e.) | Configuration | E-value |
|---|---|---|---|---|---|
| o-Toluic acid | 16.5 | 59.8 | 97.9 | (S) | 21 |
| p-Toluic acid | 19.5 | 35.8 | 29.8 | (S) | 4 |
| Benzoic acid | 17 | 25.6 | 28.4 | (S) | 14 |
| Pivalic acid | 15 | 62.4 | 99.6 | (S) | 23 |
| Cyclohexane-carboxylic acid | 16.5 | 59.4 | 97.0 | (S) | 20 |

Example 7

In a 200-ml four-necked flask equipped with a stirrer and a thermometer, 4.5 g (13.1 m mol) of (±)-4-[4-dimethylamino-1-(4'-fluorophenyl)-1-hydroxybutyl]-3-hydroxymethylbenzonitrile was dissolved in 30 ml of toluene, then 0.90 g of Novozym 435 (product of Novozymes), 2.68 g (26.2 m mol) of pivalic acid and 0.900 to 1.500 g (0.6 to 1.0 eq.) of vinyl butyrate were added, and stirred at 40° C. for 24 hours. The results are shown in Table 6.

TABLE 6

| Equivalent of Vinyl butyrate | Conversion (%) | Optical purity (% e.e.) | Configuration | E-value |
|---|---|---|---|---|
| 0.6 | 45.8 | 73.8 | (S) | 32 |
| 0.8 | 54.4 | 95.9 | (S) | 35 |
| 1.0 | 54.8 | 96.5 | (S) | 35 |

Example 8

In a 500-ml separable flask equipped with a stirrer and a thermometer, 20.0 g (58.4 mmol) of (±)-4-(4-dimethylamino-1-(4'-fluorophenyl)-1-hydroxybutyl)-3-hydroxymethylbenzonitrile was dissolved in 144 ml of toluene, then pivalic acid (1.1 to 3 eq.), 4.0 g of Novozym 435 (product of Novozymes) and 6.67 g (58.4 m mol) of vinyl butyrate were added, and stirred at 40° C. for 20 to 24 hours in a flow of nitrogen (5 ml/min). The results are shown in Table 7.

TABLE 7

| quivalent of Pivalic acid | Reaction time (hrs) | Conversion (%) | Optical purity (% e.e.) | Configuration | E-value |
|---|---|---|---|---|---|
| 0 | 21.5 | 70.7 | 98.0 | (S) | 9 |
| 1.1 | 21 | 59.9 | 98.2 | (S) | 21 |
| 1.5 | 20 | 58.0 | 98.0 | (S) | 26 |
| 2.0 | 21 | 56.9 | 98.0 | (S) | 31 |
| 3.0 | 24 | 55.2 | 97.3 | (S) | 35 |

Example 9

A test tube equipped with a stopper was charged with 10 mg (0.029 m mol) of (±)-4-[4-dimethylamino-1-(4'-fluorophenyl)-1-hydroxybutyl]-3-hydroxymethylbenzonitrile, 10 mg of Novozym 435 (product of Novozymes), 0.29 m mol of various kinds of acyl donor and 1 ml of diisopropyl ether, and stirred at 30° C. for 16 hours. For the substrate with the optical purity of at least 30% ee, E-values were calculated. The results are shown in Table 8.

TABLE 8

| Acyl donor | Conversion (%) | Optical purity (% e.e.) | Configuration | E-value |
|---|---|---|---|---|
| Vinyl acetate | 55.0 | 35.9 | (S) | 3 |
| Vinyl propionate | 46.8 | 53.9 | (S) | 7 |
| Vinyl butyrate | 66.3 | 98.3 | (S) | 13 |
| Vinyl caproate | 4.6 | | | |
| n-Butyric anhydride | 69.0 | 76.7 | (S) | 4 |
| iso-Valeric anhydride | 38.6 | 5.80 | (S) | |
| iso-Butyric anhydride | 32.5 | 3.30 | (S) | |

Example 10

A test tube equipped with a stopper was charged with 10 mg (0.029 m mol) of (±)-4-[4-dimethylamino-1-(4'-fluorophenyl)-1-hydroxybutyl]-3-hydroxymethylbenzonitrile, 10 mg of Novozym 435 (product of Novozymes), 33 mg (0.29 m mol) of vinyl butyrate and 1 ml of various kinds of solvents, and stirred at 30° C. for 16 hours. After the reaction, converted ratios and optical purities were analyzed and E-values were calculated. The results are shown in Table 9.

TABLE 9

| Solvent | Conversion (%) | Optical purity (% e.e.) | Configuration | E-value |
|---|---|---|---|---|
| tert-Butyl methyl ether | 59.3 | 91.8 | (S) | 14 |
| 1,4-Dioxane | 11.1 | | | |
| Tetrahydrofuran | 6.19 | | | |
| Diisopropyl ether | 66.3 | 98.3 | (S) | 13 |
| Diethyl ether | 59.7 | 95.8 | (S) | 17 |
| Acetone | 11.8 | | | |
| Methyl isobutyl ketone | 33.0 | | | |
| Ethanol | 7.09 | | | |
| Butanol | 6.56 | | | |
| Ethyl acetate | 10.8 | | | |
| Butyl acetate | 11.7 | | | |
| Toluene | 52.9 | 93.7 | (S) | 38 |
| Hexane | 40.7 | | | |
| Dichloroethane | 13.8 | | | |
| Acetonitrile | 25.5 | | | |
| Dimethylformamide | 5.83 | | | |
| Dimethylsulfoxide | 8.78 | | | |
| Vinyl butyrate | 57.0 | 95.0 | (S) | 22 |

Example 11

A 200-ml four-necked flask equipped with stirrer and thermometer was charged with 0.9 to 1.35 g (E/S ratios are 0.2 to 0.3) of Novozym 435 (product of Novozym). A solution of 4.5 g (13.1 mmol) of (±)-4-[4-dimethylamino-1-(4'-fluorophenyl)-1-hydroxybutyl]-3-hydroxymethylbenzonitrile in 30 ml of toluene, 2.01 g of pivalic acid (19.7 m mol), and 1.50 g (13.1 m mol) of vinyl butyrate was added into the flask, and stirred at between 35 and 45° C. for 21 hours. After the reaction, reaction fluid was separated by decantation, and the remaining enzyme was washed with 30 ml of toluene and recovered. The same operation as described above except for using the recovered enzyme was repeated four times to carry out the recycle reaction. Enzyme activities were calculated according to the following equation. The results are shown in Table 10.

Enzyme activity (U/g)=(Product amount produced per minute (μmol/min))/(Enzyme weight (g))

TABLE 10

| Batches | Enzyme activity (U/g) | | |
|---|---|---|---|
| | 35° C. (E/S = 0.30) | 40° C. (E/S = 0.25) | 45° C. (E/S = 0.20) |
| 1 | 8.61 | 12.75 | 17.37 |
| 2 | 10.31 | 12.93 | 17.70 |
| 3 | 9.75 | 12.50 | 15.48 |
| 4 | 9.39 | 12.16 | 15.06 |
| 5 | 9.01 | 11.14 | 13.10 |

Example 12

(S)-4-[4-Dimethylamino-1-(4'-fluorophenyl)-1-hydroxybutyl]-3-hydroxymethyl-benzonitrile pivalic acid salt A four-necked flask equipped with stirrer and thermometer was charged with 66.6 g of a solution of 10.0 g (0.029 mol) of (±)-4-[4-dimethylamino-1-(4'-fluorophenyl)-1-hydroxybutyl]-3-hydroxymethylbenzonitrile in toluene, and the temperature thereof was controlled so as to be 40° C. Then, 2.27 g (0.029 mol) of pyridine, 2.98 g (0.029 mol) of pivalic acid, 3.35 g (0.029 mol) of vinyl butyrate, and 2.0 g of an immobilized enzyme (Novozym 435) was added into the above mixture. The reaction mixture was stirred at 40° C. for 15 hours under a slight flow of nitrogen and stirring was stopped. The enzyme was filtrated from the reaction mixture with Kiriyama funnel, and the enzyme was washed with 21.6 g of toluene. As a result, it was obtained (S)-4-[4-dimethylamino-1-(4'-fluorophenyl)-1-hydroxybutyl]-3-hydroxymethylbenzonitrile (3.6 g, 0.011 mol, yield: 36.0%, optical purity: 98.5% ee), pivalic acid salt. The combined toluene layer was washed three times with water (50 ml, 30 ml, 30 ml) at 20° C., and an aqueous layer containing (S)-4-[4-dimethylamino-1-(4'-fluorophenyl)-1-hydroxybutyl]-3-hydroxymethylbenzonitrile (3.5 g, 0.011 mol, extraction yield: 95%), pivalic acid salt was obtained.

Example 13

(S)-4-[4-Dimethylamino-1-(4'-fluorophenyl)-1-hydroxybutyl]-3-hydroxymethyl-benzonitrile pivalic acid salt A four-necked flask equipped with stirrer and thermometer was charged with 66.7 g of a solution of 20.0 g (0.058 mol) of (±)-4-[4-dimethylamino-1-(4'-fluorophenyl)-1-hydroxybutyl]-3-hydroxymethylbenzonitrile in toluene, and the temperature thereof was controlled so as to be 40° C. Then, 5.93 g (0.058 mol) of pivalic acid, 6.62 g (0.058 mol) of vinyl butyrate, and 4.1 g of an immobilized enzyme (Novozym 435) was added into the above mixture. The reaction mixture was stirred at 40° C. for 18 hours under a slight flow of nitrogen and stirring was stopped. The enzyme was filtrated from the reaction mixture with Kiriyama funnel, and the enzyme was washed with 41.3 g of toluene. As a result, 6.7 g (0.020 mol) of (S)-4-[4-dimethylamino-1-(4'-fluorophenyl)-1-hydroxybutyl]-3-hydroxymethylbenzonitrile, pivalic acid salt was obtained in the toluene solution, with a yield of 33.5% and an optical purity of 99.7% ee.

Example 14

(S)-4-[4-Dimethylamino-1-(4'-fluorophenyl)-1-hydroxybutyl]-3-hydroxymethyl-benzonitrile cyclohexanecarboxylic acid salt A four-necked flask equipped with stirrer and thermometer was charged with 250.0 g of a solution of 25.0 g (0.073 mol) of (±)-4-[4-dimethylamino-1-(4'-fluorophenyl)-1-hydroxybutyl]-3-hydroxymethylbenzonitrile in toluene, and the temperature thereof was controlled so as to be 40° C. Then, 5.77 g (0.073 mol) of pyridine, 8.33 g (0.073 mol) of vinyl butyrate, 9.52 g (0.073 mol) of cyclohexanecarboxylic acid, and 5.0 g of an immobilized enzyme (Novozym 435) was added into the above mixture. The reaction mixture was stirred at 40° C. for 17.5 hours under a slight flow of nitrogen and stirring was stopped. The enzyme was filtrated, and washed with 54.1 g of toluene. As a result, a toluene layer containing (S)-4-[4-dimethylamino-1-(4'-fluorophenyl)-1-hydroxybutyl]-3-hydroxymethylbenzonitrile (8.6 g, 0.025 mol, yield: 34.4%, optical purity: 98.7% ee), cyclohexanecarboxylic acid salt was obtained.

The combined toluene layer was washed five times with water (187.5 ml×5) at 20° C., and an aqueous layer containing (S)-4-[4-dimethylamino-1-(4'-fluorophenyl)-1-hydroxybutyl]-3-hydroxymethylbenzonitrile (7.6 g, 0.0221 mol, extraction yield: 89%), cyclohexanecarboxylic acid salt was obtained.

Example 15

(S)-4-[4-Dimethylamino-1-(4'-fluorophenyl)-1-hydroxybutyl]-3-hydroxymethyl-benzonitrile o-toluic acid salt A four-necked flask equipped with stirrer and thermometer was charged with 250.0 g of a solution of 25.0 g (0.073 mol) of (±)-4-[4-dimethylamino-1-(4'-fluorophenyl)-1-hydroxybutyl]-3-hydroxymethylbenzonitrile in toluene, and the temperature thereof was controlled so as to be 40° C. Then, 5.77 g (0.073 mol) of pyridine, 8.33 g (0.073 mol) of vinyl butyrate, 9.93 g (0.073 mol) of o-toluic acid, and 5.0 g of an immobilized enzyme (Novozym 435) was added into the above mixture. The reaction mixture was stirred at 40° C. for 21 hours under a slight flow of nitrogen, and then stirring was stopped. The enzyme was filtrated from the reaction mixture with Kiriyama funnel, and washed with 54.1 g of toluene. As a result, a toluene layer containing (S)-4-[4-dimethylamino-1-(4'-fluorophenyl)-1-hydroxybutyl]-3-hydroxymethylbenzonitrile (9.7 g, 0.028 mol, yield: 38.8%, optical purity: 97.8% ee), o-toluic acid salt was obtained.

The combined toluene layer was washed three times with water (250 ml, 63 ml, 63 ml) at 60° C., and an aqueous layer containing (S)-4-[4-dimethylamino-1-(4'-fluorophenyl)-1-hydroxybutyl]-3-hydroxymethylbenzonitrile (7.8 g, 0.0228 mol, extraction yield: 80%), o-toluic acid salt was obtained.

Example 16

(S)-4-[4-Dimethylamino-1-(4'-fluorophenyl)-1-hydroxybutyl]-3-hydroxymethyl-benzonitrile isobutyric acid salt A four-necked flask equipped with stirrer and thermometer was charged with 33.3 g of a solution of 10.0 g (0.029 mol) of (±)-4-[4-dimethylamino-1-(4'-fluorophenyl)-1-hydroxybutyl]-3-hydroxymethylbenzonitrile in toluene, and the temperature thereof was controlled so as to be 40° C. Then, 2.29 g (0.029 mol) of pyridine, 2.57 g (0.029 mol) of iso-butyric acid, 3.33 g (0.029 mol) of vinyl butyrate, and 2.0 g of an immobilized enzyme (Novozym 435) was added into the above mixture. The reaction mixture was stirred at 40° C. for 24 hours under a slight flow of nitrogen and stirring was stopped. The enzyme was filtrated off from the reaction mixture with Kiriyama funnel, and washed with 21.6 g of toluene.

As a result, a toluene layer containing (S)-4-[4-dimethylamino-1-(4'-fluorophenyl)-1-hydroxybutyl]-3-hydroxymethylbenzonitrile (3.8 g, 0.011 mol, yield: 38.0%, optical purity: 95.9% ee), isobutyric acid salt was obtained.

Example 17

(S)-4-[4-Dimethylamino-1-(4'-fluorophenyl)-1-hydroxybutyl]-3-hydroxymethyl-benzonitrile benzoic acid salt A four-necked flask equipped with stirrer and thermometer was charged with 250.0 g of a solution of 50.0 g (0.146 mol) of (±)-4-[4-dimethylamino-1-(4'-fluorophenyl)-1-hydroxybutyl]-3-hydroxymethylbenzonitrile in toluene, and the temperature thereof was controlled so as to be 40° C. Then, 11.5 g (0.146 mol) of pyridine, 33.2 g (0.291 mol) of vinyl butyrate, 17.8 g (0.146 mol) of benzoic acid, and 10.0 g of an immobilized enzyme (Novozym 435) was added into the above mixture. The reaction mixture was stirred at 40° C. for 20 hours under a slight flow of nitrogen, and then stirring was stopped. The enzyme was filtrated from the reaction mixture with Kiriyama funnel, and washed with 108 g of toluene. As a result, a toluene layer containing (S)-4-[4-dimethylamino-1-(4'-fluorophenyl)-1-hydroxybutyl]-3-hydroxymethylbenzonitrile (22.0 g, 0.064 mol, yield: 44.0%, optical purity: 99.0% ee), benzoic acid salt was obtained.

The combined toluene layer was washed three times with water (500 ml×3) at 60° C., and an aqueous layer containing (S)-4-[4-dimethylamino-1-(4'-fluorophenyl)-1-hydroxybutyl]-3-hydroxymethylbenzonitrile (21.0 g, 0.0614 mol, extraction yield: 96%), benzoic acid salt was obtained.

The following examples 18 to 28 illustrate the separation of S-diol from the reaction mixture.

Example 18

A test tube equipped with a stopper was charged with 4.3 mg (0.0126 mmol) of (S)-4-[4-dimethylamino-1-(4'-fluorophenyl)-1-hydroxybutyl]-3-hydroxymethylbenzonitrile (compound A), 6.8 mg (0.0165 mmol) of (R)-5-cyano-2-[4-dimethylamino-1-(4'-fluorophenyl)-1-hydroxybutyl]-benzyl butyrate (compound B), 1 ml of toluene, 1 ml of water, and 0.291 m mol of various kinds of acids (in the case of a dibasic acid, 0.146 m mol is used), and stirred at 40° C. for 1 hour. Thus-obtained mixed solvent was separated into aqueous layer and toluene layer, and then the concentrations of compound A and B in each layer were measured. Partition coefficients Ka or Kb are calculated according to the following equation. The results are shown in Table 11.

$Ka$=(Concentration of the compound $A$ in aqueous layer)/(Concentration of the compound $A$ in toluene layer)

$Kb$=(Concentration of the compound $B$ in aqueous layer)/(Concentration of the compound $B$ in toluene layer)

TABLE 11

| Acid | Partition coefficient | | |
|---|---|---|---|
| | Ka | Kb | Ka/Kb |
| o-Nitrobenzoic acid | 30.7 | 0.45 | 68.3 |
| m-Nitrobenzoic acid | 19.5 | 0.08 | 237 |
| Salicylic acid | 13.0 | 0.06 | 212 |

TABLE 11-continued

| Acid | Partition coefficient | | |
|---|---|---|---|
| | Ka | Kb | Ka/Kb |
| p-Hydroxybenzoic acid | 70.8 | 0.31 | 226 |
| o-Chlorobenzoic acid | 22.8 | 0.30 | 76.7 |
| m-Chlorobenzoic acid | 4.98 | 0.04 | 122 |
| p-Chlorobenzoic acid | 7.01 | 0.06 | 123 |
| p-Fluorobenzoic acid | 14.4 | 0.12 | 120 |
| p-Ethylbenzoic acid | 2.28 | 0.03 | 73.0 |
| o-Toluic acid | 9.11 | 0.05 | 172 |
| m-Toluic acid | 6.00 | 0.03 | 215 |
| p-Toluic acid | 5.97 | 0.02 | 249 |
| o-Methoxybenzoic acid | 27.1 | 0.38 | 71.1 |
| m-Methoxybenzoic acid | 9.23 | 0.07 | 136 |
| p-Methoxybenzoic acid | 12.3 | 0.10 | 122 |
| 4-Biphenylcarboxylic acid | 0.87 | 0.04 | 24.9 |
| 3-Phenylpropionic acid | 5.67 | 0.02 | 229 |
| Benzoic acid | 18.4 | 0.08 | 244 |
| Isobutyric acid | 39.2 | 0.17 | 225 |
| Isovaleric acid | 24.4 | 0.10 | 241 |
| Pivalic acid | 9.03 | 0.10 | 92.6 |
| Caproic acid | 5.04 | 0.03 | 181 |
| Cyclohexanecarboxylic acid | 3.89 | 0.03 | 168 |
| Phthalic acid | 20.8 | 0.33 | 63.8 |
| Isophthalic acid | 7.43 | 0.29 | 25.4 |
| Terephthalic acid | 16.8 | 0.15 | 113 |
| p-Toluenesulfonic acid | 164 | 3.61 | 45.4 |
| Malonic acid | 38.5 | 1.29 | 29.8 |
| Oxalic acid | 1092 | 5.73 | 190 |
| Succinic acid | 24.1 | 0.44 | 54.6 |
| Maleic acid | 31.1 | 1.03 | 30.0 |
| None | 0.17 | 0.08 | 2.2 |

Example 19

(S)-4-[4-Dimethylamino-1-(4'-fluorophenyl)-1-hydroxybutyl]-3-hydroxymethyl-benzonitrile pivalic acid salt The enzyme was filtrated from the enzyme reaction mixture obtained by the method according to Example 1, and washed twice with toluene. Thus-obtained 1174.3 g of a toluene solution containing (S)-4-[4-dimethylamino-1-(4'-fluorophenyl)-1-hydroxybutyl]-3-hydroxymethylbenzonitrile (44.8 g, 0.131 mol), pivalic acid salt was added 600.3 g of water and extracted. Further twice extraction with 359.7 g of water gave 1375.9 g of an aqueous solution of (S)-4-[4-dimethylamino-1-(4'-fluorophenyl)-1-hydroxybutyl]-3-hydroxymethylbenzonitrile, pivalic acid salt. The aqueous solution contained 43.8 g (0.128 mol, yield: 97.8%) of (S)-4-[4-dimethylamino-1-(4'-fluorophenyl)-1-hydroxybutyl]-3-hydroxymethylbenzonitrile. Optical purity: 98.4% ee, (R)-5-cyano-2-[dimethylamino-(4'-fluorophenyl)-hydroxybutyl] benzyl butyrate: 10.7 area %.

Example 20

(S)-4-[4-Dimethylamino-1-(4'-fluorophenyl)-1-hydroxybutyl]-3-hydroxymethyl-benzonitrile pivalic acid salt To 12.6 g of an aqueous solution of (S)-4-[4-dimethylamino-1-(4'-fluorophenyl)-1-hydroxybutyl]-3-hydroxymethylbenzonitrile pivalic acid salt {content of (S)-4-[4-dimethylamino-1-(4'-fluorophenyl)-1-hydroxybutyl]-3-hydroxymethylbenzonitrile: 0.4 g, 1.168 mmol}, which was separately obtained according to the method of Example 19, was added with 1.4 g (0.018 mol) of ammonium acetate. Then 1.0 g of toluene was added therein and the mixture was stirred for 10 minutes. After standing for 30 minutes, the organic layer was discarded by separating the mixture solution, and an aqueous layer containing (S)-4-[4-dimethylamino-1-(4'-fluorophenyl)-1-hydroxybutyl]-3-hydroxymethylbenzonitrile (0.389 g, 1.136 mmol, yield: 97.3%), pivalic acid salt was obtained. By HPLC analysis, it was found that chemical purity was 97.3 area % and (R)-5-cyano-2-[dimethylamino-(4'-fluorophenyl)-hydroxybutyl]benzyl butyrate: 1.5 area % was contained.

Example 21

(S)-4-[4-Dimethylamino-1-(4'-fluorophenyl)-1-hydroxybutyl]-3-hydroxymethyl-benzonitrile pivalic acid salt To 12.6 g of an aqueous solution of (S)-4-[4-dimethylamino-1-(4'-fluorophenyl)-1-hydroxybutyl]-3-hydroxymethylbenzonitrile pivalic acid salt {content of (S)-4-[4-dimethylamino-1-(4'-fluorophenyl)-1-hydroxybutyl]-3-hydroxymethylbenzonitrile: 0.4 g, 1.168 mmol}, which was separately obtained according to the method of Example 19, was added with 1.4 g (0.013 mol) of lithium sulfate. Then 1.0 g of toluene was added therein and the mixture was stirred for 10 minutes. After standing for 30 minutes, the organic layer was discarded by separating the mixture solution, and an aqueous layer containing (S)-4-[4-dimethylamino-1-(4'-fluorophenyl)-1-hydroxybutyl]-3-hydroxymethylbenzonitrile, pivalic acid salt (0.394 g, 1.151 mmol, yield: 98.5%) was obtained. By HPLC analysis, it was found that chemical purity was 93.7 area % and (R)-5-cyano-2-[dimethylamino-(4'-fluorophenyl)-hydroxybutyl]benzyl butyrate: 5.5 area % was contained.

Example 22

(S)-4-[4-Dimethylamino-1-(4'-fluorophenyl)-1-hydroxybutyl]-3-hydroxymethyl-benzonitrile pivalic acid salt To 12.6 g of an aqueous solution of (S)-4-[4-dimethylamino-1-(4'-fluorophenyl)-1-hydroxybutyl]-3-hydroxymethylbenzonitrile pivalic acid salt {content of (S)-4-[4-dimethylamino-1-(4'-fluorophenyl)-1-hydroxybutyl]-3-hydroxymethylbenzonitrile: 0.4 g, 1.168 mmol}, which was separately obtained according to the method of Example 19, was added with 1.4 g (0.011 mol) of ammonium sulfate. Then 1.0 g of toluene was added therein and the mixture was stirred for 10 minutes. After standing for 30 minutes, the organic layer was discarded by separating the mixture solution, and an aqueous layer containing (S)-4-[4-dimethylamino-1-(4'-fluorophenyl)-1-hydroxybutyl]-3-hydroxymethylbenzonitrile, pivalic acid salt (0.397 g, 1.159 mmol, yield: 99.3%) was obtained. By HPLC analysis, it was found that chemical purity was 94.7 area % and (R)-5-cyano-2-[dimethylamino-(4'-fluorophenyl)-hydroxybutyl]benzyl butyrate: 4.5 area %, was contained.

Example 23

(S)-4-[4-Dimethylamino-1-(4'-fluorophenyl)-1-hydroxybutyl]-3-hydroxymethyl-Benzonitrile pivalic acid salt To 12.6 g of an aqueous solution of (S)-4-[4-dimethylamino-1-(4'-fluorophenyl)-1-hydroxybutyl]-3-hydroxymethylbenzonitrile pivalic acid salt {content of (S)-4-[4-dimethylamino-1-(4'-fluorophenyl)-1-hydroxybutyl]-3-hydroxymethylbenzonitrile: 0.4 g, 1.168 mmol}, which was separately obtained according to the method of Example 19, was added with 1.4 g (0.0099 mol) of sodium sulfate. Then 1.0 g of toluene was added therein and the mixture was stirred for 10 minutes. After standing for 30 minutes, the organic layer was discarded by separating the mixture solution, and an aqueous layer containing pivalic acid salt of (S)-4-[4-dimethylamino-1-(4'-fluorophenyl)-1-hydroxybutyl]-3-hydroxymethylbenzonitrile (0.391 g, 1.142 mmol, yield: 97.8%) was obtained. By HPLC analysis, it was found that chemical purity was 94.5 area % and (R)-5-cyano-2-[dimethylamino-(4'-fluorophenyl)-hydroxybutyl]benzyl butyrate: 4.7 area % was contained.

Example 24

(S)-4-[4-Dimethylamino-1-(4'-fluorophenyl)-1-hydroxybutyl]-3-hydroxymethyl-benzonitrile pivalic acid salt To 12.6 g of an aqueous solution of (S)-4-[4-dimethylamino-1-(4'-fluorophenyl)-1-hydroxybutyl]-3-hydroxymethylbenzonitrile pivalic acid salt {content of (S)-4-[4-dimethylamino-1-(4'-fluorophenyl)-1-hydroxybutyl]-3-hydroxymethylbenzonitrile: 0.4 g, 1.168 mmol}, which was separately obtained according to the method of Example 19, was added with 0.7 g (0.012 mol) of sodium chloride. Then 1.0 g of toluene was added therein and the mixture was stirred for 10 minutes. After standing for 30 minutes, the organic layer was discarded by separating the mixture solution, and an aqueous layer containing pivalic acid salt of (S)-4-[4-dimethylamino-1-(4'-fluorophenyl)-1-hydroxybutyl]-3-hydroxymethylbenzonitrile (0.397 g, 1.159 mmol, yield 99.3%) was obtained. By HPLC analysis, it was found that chemical purity was 93.3 area % and (R)-5-cyano-2-[dimethylamino-(4'-fluorophenyl)-hydroxybutyl]benzyl butyrate: 5.8 area % was contained.

Example 20-24 compared to example 19 show that the separation improves by the addition of salts.

Example 25

(S)-4-[4-Dimethylamino-1-(4'-fluorophenyl)-1-hydroxybutyl]-3-hydroxymethyl-benzonitrile pivalic acid salt The enzyme was filtrated from the enzyme reaction mixture obtained by the method according to Example 1, and washed twice with toluene. Thus-obtained 19.4 g of a toluene solution containing 1.0 g (2.92 mmol) of (S)-4-[4-dimethylamino-1-(4'-fluorophenyl)-1-hydroxybutyl]-3-hydroxymethylbenzonitrile, pivalic acid was adjusted so as to be 40° C. and 13 mL of water was added to the solution and extracted. The solution was further extracted twice with 7.5 mL of water, to obtain a solution of (S)-4-[4-dimethylamino-1-(4'-fluorophenyl)-1-hydroxybutyl]-3-hydroxymethylbenzonitrile, pivalic acid salt. In the above aqueous solution, 0.886 g (2.588 mmol, yield: 88.6%) of (S)-4-[4-dimethylamino-1-(4'-fluorophenyl)-1-hydroxybutyl]-3-hydroxymethylbenzonitrile was contained.

Example 26

(S)-4-[4-Dimethylamino-1-(4'-fluorophenyl)-1-hydroxybutyl]-3-hydroxymethyl-benzonitrile pivalic acid salt The enzyme was filtrated from the enzyme reaction mixture obtained by the method according to Example 1, and washed twice with toluene. Thus-obtained 19.4 g of a toluene solution containing 1.0 g (2.920 mmol) of (S)-4-[4-dimethylamino-1-(4'-fluorophenyl)-1-hydroxybutyl]-3-hydroxymethylbenzonitrile, pivalic acid was adjusted so as to be 40° C. and 11.6 mL of water was added to the solution and extracted. The solution was extracted further three times with 5.8 mL of water to obtain a solution of (S)-4-[4-dimethylamino-1-(4'-fluorophenyl)-1-hydroxybutyl]-3-hydroxymethylbenzonitrile, pivalic acid salt. In the above aqueous solution, 0.879 g (2.567 mmol, yield 87.9%) of (S)-4-[4-dimethylamino-1-(4'-fluorophenyl)-1-hydroxybutyl]-3-hydroxymethylbenzonitrile was contained.

Example 27

(S)-4-[4-Dimethylamino-1-(4'-fluorophenyl)-1-hydroxybutyl]-3-hydroxymethyl-benzonitrile pivalic acid salt The enzyme was filtrated from the enzyme reaction mixture obtained by the method according to Example 1, and washed twice with toluene. Thus-obtained 10.4 g of toluene solution containing 1.0 g (2.92 mmol) of (S)-4-[4-dimethylamino-1-(4'-fluorophenyl)-1-hydroxybutyl]-3-hydroxymethylbenzonitrile, pivalic acid was added 13.0 mL of water and extracted. The solution was extracted further twice with 7.5 mL of water to obtain an aqueous solution of (S)-4-[4-dimethylamino-1-(4'-fluorophenyl)-1-hydroxybutyl]-3-hydroxymethylbenzonitrile, pivalic acid salt. In the above aqueous solution, 0.954 g (2.786 mmol, yield 95.4%) of (S)-4-[4-dimethylamino-1-(4'-fluorophenyl)-1-hydroxybutyl]-3-hydroxymethylbenzonitrile was contained.

Example 28

(S)-4-[4-Dimethylamino-1-(4'-fluorophenyl)-1-hydroxybutyl]-3-hydroxymethyl-benzonitrile pivalic acid salt The enzyme was filtrated from the enzyme reaction mixture obtained by the method according to Example 1, and washed twice with toluene. Thus-obtained 19.4 g of a toluene solution containing 1.0 g (2.90 mmol) of (S)-4-[4-dimethylamino-1-(4'-fluorophenyl)-1-hydroxybutyl]-3-hydroxymethylbenzonitrile, pivalic acid salt was added with 0.43 g (4.210 mmol) of pivalic acid and the mixture was extracted with 13.0 mL of water. The solution was further extracted twice with 7.5 mL of water to obtain an aqueous solution of (S)-4-[4-dimethylamino-1-(4'-fluorophenyl)-1-hydroxybutyl]-3-hydroxymethylbenzonitrile, pivalic acid salt. In the above aqueous solution, 0.947 g (2.766 mmol, yield: 94.7%) of (S)-4-[4-dimethylamino-1-(4'-fluorophenyl)-1-hydroxybutyl]-3-hydroxymethylbenzonitrile was contained.

A comparison of example 25, 26, 27 and 28 show that an improved separation is obtained by addition of pivalic acid whereas more washings and regulation of the temperature does not have great influence on the separation.

Example 29

(S)-4-[4-Dimethylamino-1-(4'-fluorophenyl)-1-hydroxybutyl]-3-hydroxymethyl-benzonitrile To a stirred solution of racemic 4-[4-Dimethylamino-1-(4-fluoro-phenyl)-1-hydroxybutyl]-3-hydroxymethyl-benzonitrile (0.29 mmol, 100 mg) and vinylbutyrate (3.9 mmol, 0.5 ml) in anhydrous 1,4-dioxane (2.5 ml) is added lipoprotein lipase *pseudomonas* sp. (160 U, 5 mg). The reaction is heated to 37° C. and followed by HPLC. After 162 hours (at a conversion of 33.9%) the enzyme is filtered off and washed with a small amount of 1,4-dioxane. The combined organic phases are evaporated in vacuo and subsequently analyzed on super critical fluid chromatography to give (R)-butyrate ester with 72% ee and (S)-diol with 28% ee.

Example 30

(S)-4-[4-Dimethylamino-1-(4'-fluorophenyl)-1-hydroxybutyl]-3-hydroxymethyl-benzonitrile To a stirred solution of racemic 4-[4-Dimethylamino-1-(4-fluoro-phenyl)-1-hydroxybutyl]-3-hydroxymethyl-benzonitrile (0.29 mmol, 100 mg) and vinylbutyrate (0.58 mmol, 73.6 µl) in anhydrous 1,4-dioxane (3.0 ml) is added lipoprotein lipase *pseudomonas* sp. (160 U, 4 mg). The reaction is heated to 37° C. and followed by HPLC. After 194 hours at a conversion of 18.7%, the enzyme is filtered off and washed with a small amount of 1,4-dioxane. The combined organic phases are evaporated in vacuo and subsequently analyzed on super critical fluid chromatography to give (R)-butyrate ester with 92% ee and (S)-diol with 14% ee. The reaction was also monitored using 1, 4 and 8 equivalent vinylbutyrate as shown in table 12.

TABLE 12

| Entry | Vinyl-butyrate | Time (h) | Conversion (%) | Ester % EE | Ester Configuration | Diol % EE | Diol Configuration |
|---|---|---|---|---|---|---|---|
| 1 | 1 eq. | 194 | 6.2 (0.5) | 79 | (R) | 5 | (S) |
| 2 | 2 eq. | 194 | 18.7 (1.0) | 92 | (R) | 14 | (S) |
| 3 | 4 eq. | 194 | 19.1 (2.0) | 86 | (R) | 14 | (S) |
| 4 | 8 eq. | 194 | 22.6 (4.0) | 86 | (R) | 15 | (S) |

(Numbers in brackets are conversion without enzyme)

Example 31

(S)-4-[4-Dimethylamino-1-(4'-fluorophenyl)-1-hydroxybutyl]-3-hydroxymethyl-benzonitrile To a stirred solution of racemic 4-[4-Dimethylamino-1-(4-fluoro-phenyl)-1-hydroxybutyl]-3-hydroxymethyl-benzonitrile (0.29 mmol, 100 mg) and vinylbutyrate (0.59 mmol, 75 µl) in anhydrous 1,4-dioxane (2.925 ml) is added lipoprotein lipase *pseudomonas* sp. (160 U, 5 mg). The reaction is heated to 50° C. and followed by HPLC. After 165 hours at a conversion of 30.4%, the enzyme is filtered off and washed with a small amount of 1,4-dioxane. The combined organic phases are evaporated in vacuo and subsequently analyzed on super critical fluid chromatography to give (R)-butyrate ester with 98.1% ee and (S)-diol with 30.3% ee. The reaction was also monitored at 25, 37 and 65° C. as shown in table 13.

TABLE 13

| Entry | Temp | Time (h) | Conversion (%) | Ester % EE | Ester Configuration | Diol % EE | Diol Configuration |
|---|---|---|---|---|---|---|---|
| 1 | 25° C. | 238 | 5.8 (0.5) | 97.9 | (R) | 5.1 | (S) |
| 2 | 37° C. | 238 | 12.5 (1.4) | 99.1 | (R) | 8.5 | (S) |
| 3 | 50° C. | 165 | 30.4 (1.9) | 98.1 | (R) | 30.3 | (S) |
| 4 | 50° C. | 238 | 32.2 (3.0) | 97.3 | (R) | 32.1 | (S) |
| 5 | 65° C. | 238 | 26.3 (7.6) | 64.1 | (R) | 21.9 | (S) |

(Numbers in brackets are conversion without enzyme)

Example 32

(S)-4-[4-Dimethylamino-1-(4'-fluorophenyl)-1-hydroxybutyl]-3-hydroxymethyl-benzonitrile To a stirred solution of racemic 4-[4-Dimethylamino-1-(4-fluoro-phenyl)-1-hydroxy-butyl]-3-hydroxymethyl-benzonitrile (0.29 mmol, 100 mg) and vinylbutyrate (0.59 mmol, 75 µl, 2. eq.) in anhydrous 1,4-dioxane (2.925 ml) is added lipoprotein lipase *pseudomonas* sp. (160 U, 4.5 mg). The reaction is heated to 50° C. and followed by HPLC. After 209 hours, the enzyme is filtered off and washed with a small amount of 1,4-dioxane. The combined organic phases are evaporated in vacuo and subsequently analyzed on super critical fluid chromatography to give (R)-butyrate ester and (S)-diol. The reaction was also monitored with (200 mg, 500 mg and 1000 mg diol and respectively 150 µl, 375 µl and 750 µl vinylbutyrate and 2.85 ml, 2.625 ml and 2.25 ml 1,4-dioxane as shown in table 14.

Tabel 14

| | | | | Ester | | Diol | |
|---|---|---|---|---|---|---|---|
| Entry | Conc. | Time (h) | Conversion (%) | % EE | Configuration | % EE | Configuration |
| 1 | 0.1 M | 209 | 30.6 (2.6) | 84.1 | (R) | 33.1 | (S) |
| 2 | 0.2 M | 209 | 32.5 (4.9) | 62.9 | (R) | 28.7 | (S) |
| 3 | 0.5 M | 209 | 50.6 (29.6) | 32.3 | (R) | 29.1 | (S) |
| 4 | 1.0 M | 209 | 69.3 (66.3) | 8.7 | (R) | 24.9 | (S) |

Example 33

(S)-4-[4-Dimethylamino-1-(4'-fluorophenyl)-1-hydroxybutyl]-3-hydroxymethyl-benzonitrile To a stirred solution of racemic 4-[4-Dimethylamino-1-(4-fluoro-phenyl)-1-hydroxy-butyl]-3-hydroxymethyl-benzonitrile (0.29 mmol, 100 mg) and vinylbutyrate (0.59 mmol, 75 µl) in anhydrous 1,4-dioxane (2.925 ml) is added lipoprotein lipase *pseudomonas* sp. (160 U, 4 mg). The reaction is heated to 50° C. and followed by HPLC. After 473 hours, the enzyme is filtered off and washed with a small amount of 1,4-dioxane. The combined organic phases are evaporated in vacuo and subsequently analyzed HPLC. The result is shown in table 15.

TABLE 15

| Entry | Added water %(w/w) | Time (h) | Conversion (%) |
|---|---|---|---|
| 1 | 0 | 473 | 33.9 |
| 2 | 0.1 | 473 | 20.1 |
| 3 | 1.0 | 473 | 0.1 |
| 4 | 10 | 473 | 0 |

Example 34

(S)-4-[4-Dimethylamino-1-(4'-fluorophenyl)-1-hydroxybutyl]-3-hydroxymethyl-benzonitrile To a stirred solution of racemic 4-[4-Dimethylamino-1-(4-fluoro-phenyl)-1-hydroxy-butyl]-3-hydroxymethyl-benzonitrile (2.9 mmol, 1000 mg) and vinylbutyrate (5.9 mmol, 750 µl) in anhydrous 1,4-dioxane (14.25 ml) is added lipoprotein lipase *pseudomonas* sp. (160 U, 20 mg). The reaction is heated to 50° C. and followed by HPLC. After 139 hours, additional 5 mg lipase was added. After 155 hours, additional 15 mg lipase was added. After 399 hours, at a conversion of 55.7% a sample was collected. The enzyme is filtered off and washed with a small amount of 1,4-dioxane. The combined organic phases are evaporated in vacuo and subsequently analyzed on super critical fluid chromatography. After 560 hours at a conversion of 62.8%, the reaction was stopped. The enzyme is filtered off and washed with a small amount of 1,4-dioxane. The combined organic phases are evaporated in vacuo and subsequently analyzed on super critical fluid chromatography. The obtained ee-values are shown in table 16.

TABLE 16

| | | | Ester | | Diol | |
|---|---|---|---|---|---|---|
| Entry | Time (h) | Conversion (%) | % EE | Configuration | % EE | Configuration |
| 1 | 399 | 55.7 | 75.7 | (R) | 79.5 | (S) |
| 2 | 560 | 62.8 | 59.5 | (R) | 94.5 | (S) |

Example 35

(S)-citalopram diol Analogues

To a stirred solution of racemic citalopram diol analogue (0.29 mmol, 100 mg) and vinylbutyrate (0.29 mmol, 37 µl) in anhydrous 1-4-dioxane (2.925 ml) is added 4-10 mg PspLL. The reaction is heated to 50 degrees celcius and followed by HPLC. After reaction was stopped, the enzyme is filtered off and washed with a small amount of toluene. The combined organic phases are evaporated in vacuo and subsequently analyzed on super critical fluid chromatography. Result is shown in table 17.

TABLE 17

| | | Time | Conversion | Ester | | Diol | |
|---|---|---|---|---|---|---|---|
| Entry | Analogue | (h) | sion (%) | % EE | Conf | % EE | Conf |
| 1 | 5-Bromo | 409 | 56.4 (8.9) | 67.1 | R | 46.3 | S |
| 2 | 5-Carboxamide | 456 | 20.5 (5.0) | 11.7 | R | 20.5 | S |
| 3 | 5-Iodo | 143 | 28.0 (1.9) | 98.9 | R | 29.9 | S |
| 4 | 5-Chloro | 244 | 30.5 (4.6) | 54.7 | R | 24.3 | S |
| 5 | 5-Formyl | 244 | 33.9 (8.3) | 88.5 | R | 13.9 | S |

(Numbers in brackets are conversion without enzyme)

Example 36

(S)-4-[4-Dimethylamino-1-(4'-fluorophenyl)-1-hydroxybutyl]-3-hydroxymethyl-benzonitrile To a stirred solution of racemic 4-[4-Dimethylamino-1-(4-fluoro-phenyl)-1-hydroxy-butyl]-3-hydroxymethyl-benzonitrile (29 mmol, 10 g) and vinylbutyrate (58 mmol, 7.5 ml) in anhydrous 1,4-dioxane (142.5 ml) is added lipoprotein lipase *pseudomonas* sp. (160 U, 250 mg). The reaction is heated to 50° C. and followed by HPLC. After 192 hours at a conversion of 41%, additional 250 mg lipase was added. After 504 hours, at a conversion of 63% the reaction was stopped. The enzyme is filtered off and washed with a small amount of 1,4-dioxane. The combined organic phases are evaporated in vacuo and subsequently analyzed on super critical fluid chromatography. Obtained EE-value ((S-diol)=95% (S-diol/R-diol=40:1).

Example 37

Isolation of (S)-4-[4-Dimethylamino-1-(4'-fluorophenyl)-1-hydroxybutyl]-3-hydroxymethyl-benzonitrile by Flash-Chromatography A mixture of 372 mg S-citalopram diol with ee-value 94.5% and 628 mg R-citalopram diol butyrate ester with ee-value 59.5% was dissolved in a minimum of ethylacetate/heptane 4:1 with 4% triethylamine. The S-citalopram diol was isolated using flash-chromatography in ethylacetate/heptane 4:1 with 4% triethylamine to obtained 120 mg S-citalopram diol (ee-value 94.5%).

Example 38

Isolation of (S)-4-[4-Dimethylamino-1-(4'-fluorophenyl)-1-hydroxybutyl]-3-hydroxymethyl-benzonitrile by Washing a Mixture Containing the S-Diol Base To a mixture of S-citalopram diol and R-citalopram diol butyrate ester (0.3 g each) was added 24 ml heptane and 66 ml water/methanol (2:1). The clear solution was transferred to a separation funnel and organic phase was collected. Additional 10 ml heptane was added to aqueous phase and mixed thoroughly. Organic phase was collected. Ekstraction repeated additional 4 times. The combined heptane phases were ekstracted with 20 ml water/methanol (2:1) and aqueous phases were combined and evaporated to half volume and extracted with 3 times 10 ml ethylacetate. The combined ethylacetate phases were dried with $Na_2SO_4$, filtered and dried in vacuo to obtaine 0.15 g S-citalopram diol containing 2% R-citalopram diol butyrate ester.

Example 39

(S)-Citalopram Diol Analogues Using Novozymes 435

To a stirred solution of racemic citalopram diol analogue (0.29 mmol, 100 mg) and vinylbutyrate (0.29 mmol, 37 µl) in anhydrous toluene (2.925 ml) is added 0.2 mg Novozymes 435 and (0.32 mmol, 33 mg) pivalic acid. The reaction is heated to 40 degrees celcius and followed by HPLC. After reaction was stopped, the enzyme is filtered off and washed with a small amount of toluene. The combined organic phases are evaporated in vacuo and subsequently analyzed on super critical fluid chromatography. Result is shown in table 18.

TABLE 18

| Entry | Analogue | Time (h) | Conversion (%) | Ester % EE | Ester Conf | Diol % EE | Diol Conf |
|---|---|---|---|---|---|---|---|
| 1 | 5-Bromo | 24 | 54 | 74.9 | R | 97.1 | S |
| 2 | 5-Carboxamide | 96 | 33 | 81.3 | R | 41.7 | S |
| 3 | 5-Iodo | 24 | 54 | 99.9 | R | 99.5 | S |
| 4 | 5-Chloro | 24 | 51 | 74.9 | R | 96.3 | S |
| 5 | 5-Formyl | 24 | 33 | 61.1 | R | 21.5 | S |

Example 40

The Influence of Various Carboxylic Acids on the Enzymatic Acylation Using Novozymes 435

To a stirred solution of racemic 4-[4-Dimethylamino-1-(4-fluoro-phenyl)-1-hydroxy-butyl]-3-hydroxymethyl-benzonitrile (0.29 mmol, 100 mg) and vinylbutyrate (0.29 mmol, 37 µl) in anhydrous toluene (2.925 ml) is added Novozymes 435, (0.2 mg) and 1.1 eq. Carboxylic acid. The reaction is heated to 40 degrees celcius and followed by HPLC. The enzyme is filtered off and washed with a small amount of toluene. The combined organic phases are evaporated in vacuo and subsequently analyzed on super critical fluid chromatography. Result is shown in table 19.

TABLE 19

| Entry | Carboxylic acid | Time (h) | Conversion (%) | Ester % EE | Ester Conf | Diol % EE | Diol Conf |
|---|---|---|---|---|---|---|---|
| 1 | Acetic acid | 24 | 18 | 92.1 | R | 65.7 | S |
| 2 | Propionic acid | 24 | 34 | 89.7 | R | 94.7 | S |
| 3 | Pivalic acid | 24 | 55 | 88.3 | R | 85.5 | S |
| 4 | Cyclohexan-carboxylic acid | 24 | 55 | 84.5 | R | 99.7 | S |
| 5 | Benzoic acid | 72 | 50 | 92.3 | R | 86.7 | S |
| 6 | Hydrocinnamic acid | 72 | 48 | 94.1 | R | 84.3 | S |
| 7 | Isovaleric acid | 48 | 51 | 88.3 | R | 90.7 | S |
| 8 | Decanoic acid | 72 | 53 | 82.9 | R | 86.9 | S |
| 9 | Isobutyric acid | 48 | 53 | 86.9 | R | 92.7 | S |
| 10 | Crotonic acid | 72 | 54 | 82.9 | R | 95.1 | S |
| 11 | 2-ethylbutyric acid | 24 | 50 | 87.1 | R | 94.3 | S |
| 12 | Palmitic acid | 48 | 54 | 71.3 | R | 93.3 | S |

Example 41

(R)-5-Cyano-2-[dimethylamino-(4'-fluorophenyl)-hydroxybutyl]benzyl butyrate

A four-necked flask equipped with stirrer and thermometer was charged with 219 g of a solution containing 21.9 g (0.064 mol) of (±)-4-[4-dimethylamino-1-(4'-fluorophenyl)-1-hydroxybutyl]-3-hydroxymethylbenzonitrile in toluene. Then, 14.6 g (0.128 mmol) of vinyl butyrate, 5.07 g (0.128 mol) of pyridine, 7.89 g (0.064 mol) of benzoic acid and 2.19 g of an immobilized enzyme (Novozym 435) were added into the above mixture. The reaction mixture was allowed to warm up to 60° C. and stirred for 15 hours under a slight flow of nitrogen and stirring was stopped. The enzyme was filtrated off from the reaction mixture with Kiriyama funnel, and washed with 50 g of toluene. The combined toluene layer was washed twice with water (255 ml, 265 ml) and concentrated to give 14.9 g of (R)-5-Cyano-2-[dimethylamino-(4'-fluorophenyl)-hydroxybutyl]benzyl butyrate benzoic acid salt.

To a mixture of 4.0 g of (R)-5-Cyano-2-[dimethylamino-(4'-fluorophenyl)-hydroxybutyl]benzyl butyrate benzoic acid salt (7.48 mmol), 40 ml of water and 40 ml of toluene were added 1.26 g of 30% sodium hydroxide (9.45 mol) with stirring, the mixture was kept stirring for 30 minutes. After stirring, the mixture was allowed to stand and the toluene layer was separated. The toluene layer was washed with 40 ml of water and concentrated at 40° C. under reduced pressure, to thereby obtain 2.7 g of (R)-5-Cyano-2-[dimethylamino-(4'-fluorophenyl)-hydroxybutyl]benzyl butyrate. 1H NMR (400 MHz. CDCl3) ä(ppm): 7.69 (1H, s), 7.68-7.56 (2H, m), 7.36-

7.23 (2H, m), 7.02-6.90 (2H, m), 5.41 (1H, d, J=14.9 Hz), 4.99 (1H, d, J=14.6 Hz), 2.59-2.42 (1H, m), 2.40-2.30 (3H, m), 2.26 (2H, dt, J=7.3 Hz, 1.5 Hz), 2.18 (6H, s), 1.68-1.57 (2H, m), 1.67-1.46 (2H, m), 0.93 (3H, t, J=7.6 Hz).

Example 42

Escitalopram,oxalate (S)-4-(4-Dimethylamino)-1-(4'-fluorophenyl)-1-hydroxybutyl)-3-hydroxymethylbenzonitrile (15.8 g, 46.2 mmol) having a chemical purity of 99% and an ee of 98.7% as determined by Chiral Supercritical Fluid Chromatography, was dissolved in toluene (100 mL). Triethylamine (13.0 mL, 93.2 mmol) was added followed by slow addition of a solution of tosyl chloride (9.4 g, 49.4 mmol) in toluene (100 mL). The resulting solution was stirred at room temperature for 20 min. then added water (50 mL) and conc. Ammonia (25 mL). The mixture was stirred at 45° C. for 2 min, transferred to a separatory funnel. The phases were separated and the organic phase was washed with water (50 mL), dried with MgSO4, filtered and concentrated under reduced pressure to give the crude product (14.2 g) in 95% yield. The crude product was dissolved in ethanol (17 mL) and was added a solution of oxalic acid (3.95 g, 43.9 mmol) in ethanol (27 mL). The precipitate was collected by filtration to give Escitalopram, oxalate (14.0 g), which was re-crystallised from ethanol (85 mL) to give the final product (12.2 g). The purity was determined to be 99.65% by HPLC. The ee was 98.5% determined by Chiral Supercritical Fluid Chromatography.

The invention claimed is:

1. A process for the preparation of escitalopram having the formula

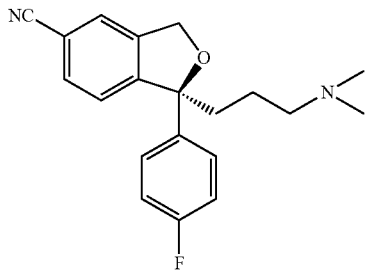

(I)

or a pharmaceutically acceptable salt thereof, comprising
(i) preparing the S-enantiomer of a diol having the formula (IIs)

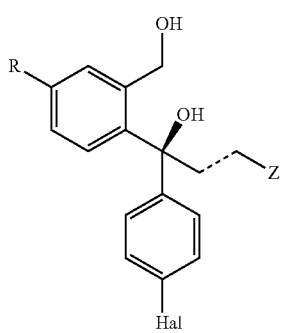

(IIs)

or a salt thereof;
wherein R is cyano or a group which may be converted to a cyano group, the dotted line represents a double or a single bond, Z is a dimethylaminomethyl group or a group which may be converted to a dimethylaminomethyl group and Hal is a halogen or (ii) preparing the S-enantiomer of an acylated diol having the formula (IVs)

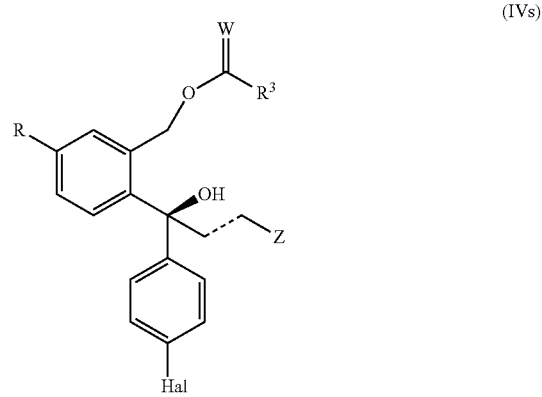

(IVs)

or a salt thereof;
wherein R, Z, the dotted line and Hal are as defined above, W is O or S, and $R^3$ is —Y—$R^1$, wherein $R^1$ is $C_{1-10}$-alkyl, $C_{2-10}$-alkenyl or $C_{2-10}$-alkynyl, all of which may optionally be substituted one or more times with substituents selected from $C_{1-10}$-alkoxy, $C_{1-10}$-alkylthio, hydroxy, halogen, amino, nitro, cyano, $C_{1-10}$-alkylamino, di-($C_{1-10}$-alkyl)amino, aryl, aryloxy, arylthio and heteroaryl, or $R^1$ is aryl, wherein any of the aryl and heteroaryl groups may optionally be substituted one or more times with substituents selected from $C_{1-10}$-alkyl, $C_{2-10}$-alkenyl, $C_{2-10}$-alkynyl, $C_{1-10}$-alkoxy, $C_{1-10}$-alkylthio, hydroxy, halogen, amino, nitro, cyano, $C_{1-10}$-alkylamino and di-($C_{1-10}$-alkyl)amino; and Y is a bond, O, S or NH
wherein the diol of formula (IIs) and/or the acylated diol of formula (IVs) is prepared by a method comprising:
(a) subjecting a racemic diol of formula (II)

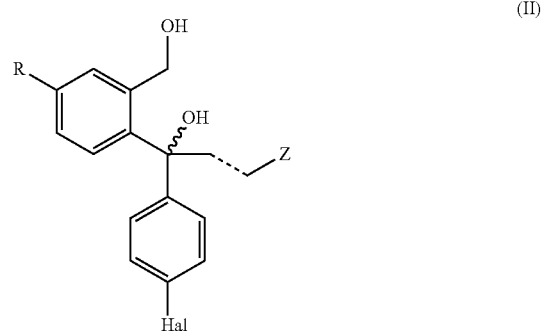

(II)

wherein R is cyano or a group which may be converted to a cyano group, Z is —$CH_2$—N(R'R") wherein R' and R" are $C_{1-6}$-alkyl, or R' and R" are connected to each other to form a cyclic structure including the N-atom to which they are attached, or Z is a group which may be converted to a dimethylaminomethyl group, the dotted line is a double or single bond, and Hal is a halogen;

to selective enzymatic acylation using an acylating agent having the formula

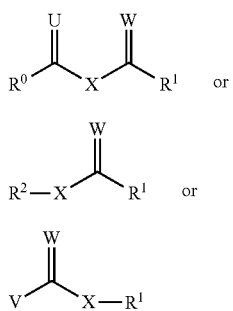

or an isocyanate having the formula $R^1$—N=C=O or an isothiocyanate having the formula $R^1$—N=C=S; wherein X is O or S; W is O or S; U is O or S; and V is halogen; provided that each of W and U is not S when X is S;

$R^0$ is $C_{1-10}$-alkyl, $C_{2-10}$-alkenyl or $C_{2-10}$-alkynyl, all of which may optionally be substituted one or more times with substituents selected from $C_{1-10}$-alkoxy, $C_{1-10}$-alkylthio, hydroxy, halogen, amino, nitro, cyano, $C_{1-10}$-alkylamino, di-($C_{1-10}$-alkyl)amino, aryl, aryloxy, arylthio and heteroaryl, or $R^0$ is aryl, wherein any of the aryl and heteroaryl groups may optionally be substituted one or more times with substituents selected from $C_{1-10}$-alkyl, $C_{2-10}$-alkenyl, $C_{2-10}$-alkynyl, $C_{1-10}$-alkoxy, $C_{1-10}$-alkylthio, hydroxy, halogen, amino, nitro, cyano, $C_{1-10}$-alkylamino and di-($C_{1-10}$-alkyl)amino;

$R^1$ is as defined above for $R^0$; or $R^0$ and $R^1$ together form a chain of 3 to 5 carbon atoms;

$R^2$ is as defined above for $R^0$, or $R^2$ is a suitable leaving group;

to form a mixture of (1) the S-enantiomer of the diol of formula (II) and the R-enantiomer of the compound of formula (IV) or (2) the R-enantiomer of the diol of formula (II) and the S enantiomer of the compound of formula (IV)

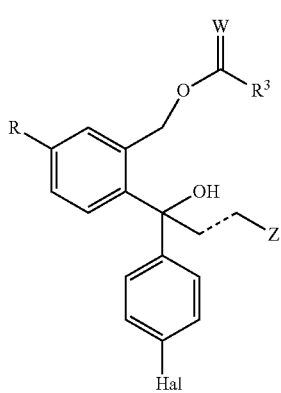

wherein R, Hal, the dotted line and Z are as defined above; wherein W is O or S, and $R^3$ is —Y—$R^1$ wherein $R^1$ is $C_{1-10}$-alkyl, $C_{2-10}$-alkenyl or $C_{2-10}$-alkynyl, all of which may optionally be substituted one or more times with substituents selected from $C_{1-10}$-alkoxy, $C_{1-10}$-alkylthio, hydroxy, halogen, amino, nitro, cyano, $C_{1-10}$-alkylamino, di-($C_{1-10}$-alkyl) amino, aryl, aryloxy, arylthio and heteroaryl, or $R^1$ is aryl, wherein any of the aryl and heteroaryl groups may optionally be substituted one or more times with substituents selected from $C_{1-10}$-alkyl, $C_{2-10}$-alkenyl, $C_{2-10}$-alkynyl, $C_{1-10}$-alkoxy, $C_{1-10}$-alkylthio, hydroxy, halogen, amino, nitro, cyano, $C_{1-10}$-alkylamino and di-($C_{1-10}$-alkyl)amino and Y is a bond, O, S or NH; or (b) subjecting a racemic compound of formula (IV)

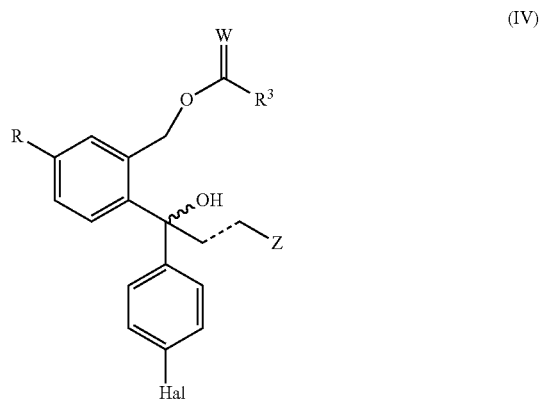

wherein R, Z, W, Hal, the dotted line and $R^3$ are as defined above; to selective enzymatic deacylation to form a mixture of the S- or R-enantiomer of a diol of formula (II)

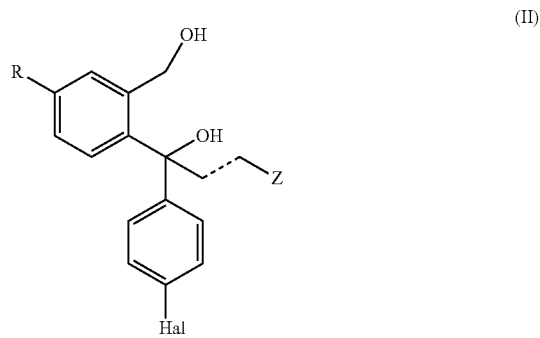

wherein R, Hal, the dotted line and Z are as defined above, and the opposite enantiomer of a compound of formula (IV); and (c) isolating, in either order, (1) the S-enantiomer of the diol of formula (II) and the R-enantiomer of the compound of formula (IV) or a salt thereof or (2) the R-enantiomer of the diol of formula (II) and the S-enantiomer of the compound of formula (IV) or a salt thereof;

(iii) optionally subjecting the diol of formula (IIs) or the acylated diol of formula (IVs) to one or more reactions, in any order, selected from (a) conversion of the group R to a cyano group,
(b) conversion of the group Z to a dimethylaminomethyl group,
(c) reduction of a double bond represented by the dotted line to a single bond and
(d) conversion of the group Hal to a fluoro group;

(iv) effecting ring closure under basic conditions of the diol of formula (IIs) or the acylated diol of formula (IVs), or a labile ester derivative thereof, to form a compound of formula (V)

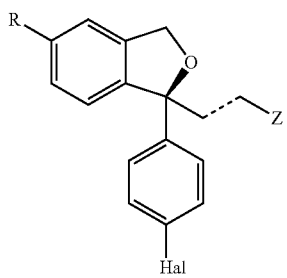

(V)

(v) subjecting the compound of formula (V) to, in any order:
  (a) conversion of the group R to a cyano group, if R is not cyano,
  (b) conversion of the group Z to a dimethylaminomethyl group, if Z is not dimethylaminomethyl,
  (c) reduction to a single bond, if the dotted line represents a double bond, and
  (d) conversion of Hal to a fluoro group, if Hal is not fluoro; and
(vi) isolating escitalopram or a pharmaceutically acceptable salt thereof.

2. The method of claim 1 wherein (1) the S-enantiomer of the diol of formula (II) and the R-enantiomer of the compound of formula (IV) or (2) the R-enantiomer of the diol of formula (II) and the S-enantiomer of the compound of formula (IV) are separated from each other by a process comprising
  (a) treating the mixture with an acid in a mixture of water and an organic solvent;
  (b) separating the aqueous phase containing the diol of formula (II) as a salt of said acid from the organic phase to obtain an organic phase containing the compound of formula (IV) as a salt of said acid;
  (c) optionally isolating the diol of formula (II) as the base or a salt thereof; and
  (d) optionally isolating the compound of formula (IV) as the base or a salt thereof.

3. The method of claim 1 wherein (1) the S-enantiomer of the diol of formula (II) and the R-enantiomer of the compound of formula (IV) or (2) the R-enantiomer of the diol of formula (II) and the S-enantiomer of the compound of formula (IV) are separated from each other by a process comprising
  a) treating the mixture with a mixture of water, a protic organic solvent and an apolar organic solvent;
  b) separating the aqueous phase containing the diol of formula (II), from the organic phase to obtain an organic phase containing the compound of formula (IV);
  c) optionally isolating the diol of formula (II) from the aqueous phase and/or the compound of formula (IV) from the organic phase; and
  d) optionally converting the diol of formula (II) and/or the compound of formula (IV) to a salt thereof.

4. A method for the preparation of racemic citalopram and/or escitalopram or a pharmaceutically acceptable salt thereof comprising (i) preparing the R-enantiomer of a diol having the formula (IIr)

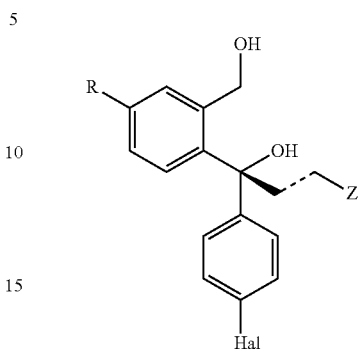

(IIr)

or a salt thereof;
  wherein R is cyano or a group which may be converted to a cyano group, the dotted line represents a double or a single bond and Z is a dimethylaminomethyl group or a group which may be converted to a dimethylaminomethyl group and Hal is a halogen, or (ii) preparing the R-enantiomer of an acylated diol having the formula (IVr)

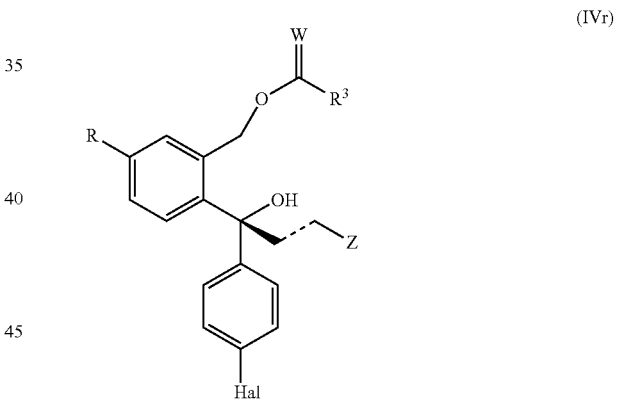

(IVr)

or a salt thereof;
  wherein R, Z, the dotted line Hal are as defined above, W is O or S, and $R^3$ is $-Y-R^1$, wherein $R^1$ is $C_{1-10}$-alkyl, $C_{2-10}$-alkenyl or $C_{2-10}$-alkynyl, all of which may optionally be substituted one or more times with substituents selected from $C_{1-10}$-alkoxy, $C_{1-10}$-alkylthio, hydroxy, halogen, amino, nitro, cyano, $C_{1-10}$-alkylamino, di-($C_{1-10}$-alkyl)amino, aryl, aryloxy, arylthio and heteroaryl, or $R^1$ is aryl, wherein any of the aryl and heteroaryl groups may optionally be substituted one or more times with substituents selected from $C_{1-10}$-alkyl, $C_{2-10}$-alkenyl, $C_{2-10}$-alkynyl, $C_{1-10}$-alkoxy, $C_{1-10}$-alkylthio, hydroxy, halogen, amino, nitro, cyano, $C_{1-10}$-alkylamino and di-($C_{1-10}$-alkyl)amino; and Y is a bond, O, S or NH, wherein the diol of formula (IIr) and/or the acylated diol of formula (IVr) is prepared by a method comprising:

(a) subjecting a racemic diol of formula (II)

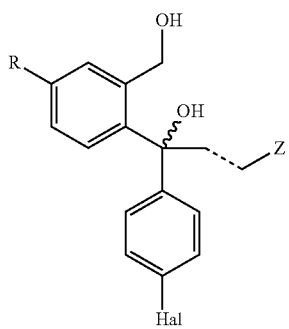
(II)

wherein R is cyano or a group which may be converted to a cyano group, Z is —CH$_2$—N(R'R") wherein R' and R" are C$_{1-6}$-alkyl, or R' and R" are connected to each other to form a cyclic structure including the N-atom to which they are attached, or Z is a group which may be converted to a dimethylaminomethyl group, the dotted line is a double or single bond, and Hal is a halogen;

to selective enzymatic acylation using an acylating agent having the formula

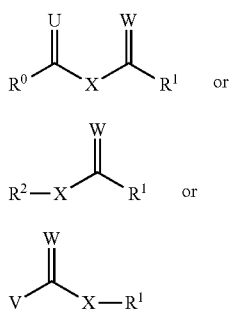
(IIIa)
or
(IIIb)
or
(IIIc)

or an isocyanate having the formula R$^1$—N=C=O or an isothiocyanate having the formula R$^1$—N=C=S; wherein X is O or S; W is O or S; U is O or S; and V is halogen; provided that each of W and U is not S when X is S;

R$^0$ is C$_{1-10}$-alkyl, C$_{2-10}$-alkenyl or C$_{2-10}$-alkynyl, all of which may optionally be substituted one or more times with substituents selected from C$_{1-10}$-alkoxy, C$_{1-10}$-alkylthio, hydroxy, halogen, amino, nitro, cyano, C$_{1-10}$-alkylamino, di-(C$_{1-10}$-alkyl)amino, aryl, aryloxy, arylthio and heteroaryl, or R$^0$ is aryl, wherein any of the aryl and heteroaryl groups may optionally be substituted one or more times with substituents selected from C$_{1-10}$-alkyl, C$_{2-10}$-alkenyl, C$_{2-10}$-alkynyl, C$_{1-10}$-alkoxy, C$_{1-10}$-alkylthio, hydroxy, halogen, amino, nitro, cyano, C$_{1-10}$-alkylamino and di-(C$_{1-10}$-alkyl)amino;

R$^1$ is as defined above for R$^0$; or R$^0$ and R$^1$ together form a chain of 3 to 5 carbon atoms;

R$^2$ is as defined above for R$^0$, or R$^2$ is a suitable leaving group;

to form a mixture of (1) the S-enantiomer of the diol of formula (II) and the R-enantiomer of the compound of formula (IV) or (2) the R-enantiomer of the diol of formula (II) and the S enantiomer of the compound of formula (IV)

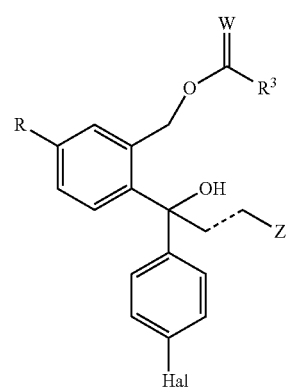
(IV)

wherein R, Hal, the dotted line and Z are as defined above;

wherein W is O or S, and R$^3$ is —Y—R' wherein R$^1$ is C$_{1-10}$-alkyl, C$_{2-10}$-alkenyl or C$_{2-10}$-alkynyl, all of which may optionally be substituted one or more times with substituents selected from C$_{1-10}$-alkoxy, C$_{1-10}$-alkylthio, hydroxy, halogen, amino, nitro, cyano, C$_{1-10}$-alkylamino, di-(C$_{1-10}$-alkyl)amino, aryl, aryloxy, arylthio and heteroaryl, or R$^1$ is aryl, wherein any of the aryl and heteroaryl groups may optionally be substituted one or more times with substituents selected from C$_{1-10}$-alkyl, C$_{2-10}$-alkenyl, C$_{2-10}$-alkynyl, C$_{1-10}$-alkoxy, C$_{1-10}$-alkylthio, hydroxy, halogen, amino, nitro, cyano, C$_{1-10}$-alkylamino and di-(C$_{1-10}$-alkyl)amino and Y is a bond, O, S or NH; or (b) subjecting a racemic compound of formula (IV)

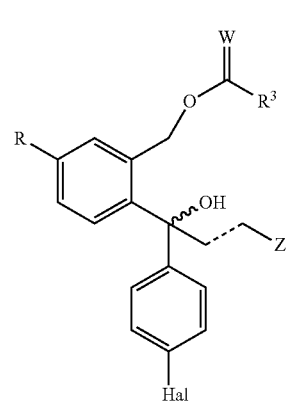
(IV)

wherein R, Z, W, Hal, the dotted line and R$^3$ are as defined above; to selective enzymatic deacylation to form a mixture of the S- or R-enantiomer of a diol of formula (II)

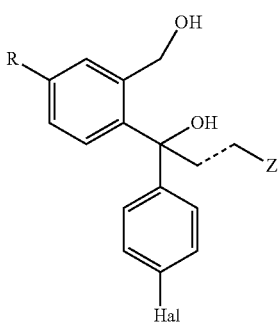

(II)

wherein R, Hal, the dotted line and Z are as defined above, and the opposite enantiomer of a compound of formula (IV); and (c) isolating, in either order, the (1) the S-enantiomer of the diol of formula (II) and the R-enantiomer of the compound of formula (IV) or a salt thereof or (2) the R-enantiomer of the diol of formula (II) and the S-enantiomer of the compound of formula (IV) or a salt thereof;

(iii) optionally subjecting the diol of formula (IIr) or the acylated diol of formula (IVr) to one or more reactions, in any order, selected from
(a) conversion of the group R to a cyano group,
(b) reduction of a double bond represented by the dotted line to a single bond,
(c) conversion of the group Z to a dimethylaminomethyl group, and
(d) conversion of the group Hal to a fluoro group;

(iv) effecting ring closure under acidic conditions of the diol of formula (IIr) or the acylated diol of formula (IVr), to form a mixture of the S-enantiomer of the compound of formula (V)

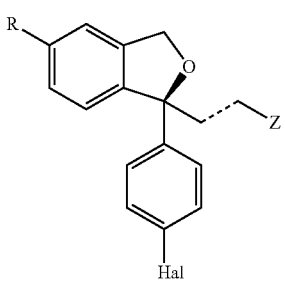

(V)

and a minor amount of the corresponding R-enantiomer;

(v) subjecting the compound of formula (V) to, in any order:
(a) conversion of the group R to a cyano group, if R is not cyano,
(b) conversion of the group Z to a dimethylaminomethyl group, if Z is not dimethylaminomethyl,
(c) reduction to form a single bond, if the dotted line represents a double bond, and
(d) conversion of Hal to a fluoro group, if Hal is not fluoro; and (vi) isolating escitalopram and/or racemic citalopram or a pharmaceutically acceptable salt thereof.

5. The method of claim 4 wherein the racemic citalopram is isolated by precipitating racemic citalopram free base or a salt thereof, and recovering escitalopram from the mother liquor of the precipitation.

6. The method of claim 4 wherein the mixture of (1) the S-enantiomer of the diol of formula (II) and the R-enantiomer of the compound of formula (IV) or (2) the R-enantiomer of the diol of formula (II) and the S-enantiomer of the compound of formula (IV) are separated from each other by a process comprising
(a) treating the mixture with an acid in a mixture of water and an organic solvent;
(b) separating the aqueous phase containing the diol of formula (II) as a salt of said acid from the organic phase to obtain an organic phase containing the compound of formula (IV) as a salt of said acid;
(c) optionally isolating the diol of formula (II) as the base or a salt thereof; and
(d) optionally isolating the compound of formula (IV) as the base or a salt thereof.

7. The method of claim 4 wherein (1) the S-enantiomer of the diol of formula (II) and the R-enantiomer of the compound of formula (IV) or (2) the R-enantiomer of the diol of formula (II) and the S-enantiomer of the compound of formula (IV) are separated from each other by a process comprising
a) treating the mixture with a mixture of water, a protic organic solvent and an apolar organic solvent;
b) separating the aqueous phase containing the diol of formula (II), from the organic phase to obtain an organic phase containing the compound of formula (IV);
c) optionally isolating the diol of formula (II) from the aqueous phase and/or the compound of formula (IV) from the organic phase; and
d) optionally converting the diol of formula (II) and/or the compound of formula (IV) to a salt thereof.

* * * * *